US012740995B2

(12) United States Patent
Yu et al.

(10) Patent No.: US 12,740,995 B2
(45) Date of Patent: Sep. 22, 2026

(54) METHODS AND COMPOSITIONS FOR TREATING NEURODEGENERATIVE DISEASES

(71) Applicant: Augusta University Research Institute, Inc., Augusta, GA (US)

(72) Inventors: Robert Yu, North Augusta, SC (US); Yutaka Itokazu, Augusta, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 494 days.

(21) Appl. No.: 18/262,174

(22) PCT Filed: Jan. 19, 2022

(86) PCT No.: PCT/US2022/012993
§ 371 (c)(1),
(2) Date: Jul. 19, 2023

(87) PCT Pub. No.: WO2022/159501
PCT Pub. Date: Jul. 28, 2022

(65) Prior Publication Data

US 2024/0100076 A1 Mar. 28, 2024

Related U.S. Application Data

(60) Provisional application No. 63/139,057, filed on Jan. 19, 2021.

(51) Int. Cl.
*A61K 31/7032* (2006.01)
*A61P 25/16* (2006.01)
*A61P 25/28* (2006.01)

(52) U.S. Cl.
CPC .......... *A61K 31/7032* (2013.01); *A61P 25/16* (2018.01); *A61P 25/28* (2018.01)

(58) Field of Classification Search
None
See application file for complete search history.

(56) References Cited

U.S. PATENT DOCUMENTS

| | | | | |
|---|---|---|---|---|
| 4,710,490 | A | 12/1987 | Catsimpoolas et al. | |
| 8,609,088 | B2 | 12/2013 | Wolf et al. | |
| 2006/0030542 | A1* | 2/2006 | Frey, II | A61K 31/7076 514/47 |
| 2011/0110957 | A1* | 5/2011 | Stamford | A61P 31/00 514/215 |
| 2012/0283199 | A1 | 11/2012 | Sipione et al. | |

FOREIGN PATENT DOCUMENTS

| | | | | |
|---|---|---|---|---|
| WO | 9107947 A1 | | 6/1991 | |
| WO | WO-2011028799 A2 | * | 3/2011 | A61M 13/003 |

OTHER PUBLICATIONS

Ledeen, R. W., & Wu, G. (2018). Gangliosides, α-Synuclein, and Parkinson's disease. Progress in molecular biology and translational science, 156, 435-454. (Year: 2018).*

Wilkinson, G. Pharmacokinetics, The Dynamics of Drug Absorption, Distribution, and Elimination (2001). In: Goodman and Gilman s the pharmacological basis of therapeutics. International edition, 10th edition, Mc Grow Hill, 971. (Year: 2001).*

Ariga, et al., Glycolipid composition of human cataractous lenses. Characterization of Lewisx glycolipids, J Biol Chem., vol. 269, No. 4, Jan. 28, 1994, pp. 2667-2675.

Baker, et al., Transneuronal transport of peroxidase-conjugated wheat germ agglutinin (WGA-HRP) from the olfactory epithelium to the brain of the adult rat, Exp Brain Res., vol. 63, No. 3, 1986, pp. 461-473.

Balin, et al., Avenues for entry of peripherally administered protein to the central nervous system in mouse, rat, and squirrel monkey, J Comp Neurol., vol. 251, No. 2, Sep. 8, 1986, pp. 260-280.

Bamford, et al., A prospective evaluation of cognitive decline in early Huntington's disease: functional and radiographic correlates, Neurology, vol. 45, No. 10, Oct. 1995, pp. 1867-1873.

Banks, et al., Brain uptake of the glucagon-like peptide-1 antagonist exendin(9-39) after intranasal administration, J Pharmacol Exp Ther., vol. 309, No. 2, May 2004, pp. 469-475.

Banks, William A., Delivery of peptides to the brain: emphasis on therapeutic development, Biopolymers, vol. 90, No. 5, 2008, pp. 589-594.

Berg, et al., Hydroxocobalamin uptake into the cerebrospinal fluid after nasal and intravenous delivery in rats and humans, J Drug Target, vol. 11, No. 6, Jul. 2003, pp. 325-331.

Berg, et al., Serial cerebrospinal fluid sampling in a rat model to study drug uptake from the nasal cavity, J Neurosci Methods, vol. 116, No. 1, Apr. 30, 2002, pp. 99-107.

Berg, et al., Uptake of melatonin into the cerebrospinal fluid after nasal and intravenous delivery: studies in rats and comparison with a human study, Pharm Res., vol. 21, No. 5, May 2004, pp. 799-802.

Born, et al., Sniffing neuropeptides: a transnasal approach to the human brain, Nat Neurosci., vol. 5, No. 6, Jun. 2002, pp. 514-516.

Boulton, et al., Contribution of extracranial lymphatics and arachnoid villi to the clearance of a CSF tracer in the rat, Am J Physiol., vol. 276, No. 3, Mar. 1999, pp. R818-R823.

Boulton, et al., Drainage of CSF through lymphatic pathways and arachnoid villi in sheep: measurement of 125I-albumin clearance, Neuropathol Appl Neurobiol., vol. 22, No. 4, Aug. 1996, pp. 325-333.

(Continued)

*Primary Examiner* — Dale R Miller
(74) *Attorney, Agent, or Firm* — PABST PATENT GROUP LLP

(57) ABSTRACT

Methods and compositions for treating neurodegenerative diseases are provided. In one embodiment, the method includes administering gangliosides into the brain of a mammal in need of such treatment. The gangliosiges are preferably GM1 and GD3 gangliosides. The gangliosides are intranasally administered in an amount effective to delay and/or prevent disease progression, and to increase the resilience of brains by promoting adult neurogenesis by gangliosides.

19 Claims, 12 Drawing Sheets

Specification includes a Sequence Listing.

(56) References Cited

OTHER PUBLICATIONS

Bradbury, et al., Drainage of cerebral interstitial fluid into deep cervical lymph of the rabbit, Am J Physiol., vol. 240, No. 4, Apr. 1981, pp. F329-F336.
Bradbury, et al., Factors influencing exit of substances from cerebrospinal fluid into deep cervical lymph of the rabbit, J Physiol., vol. 339, Jun. 1983, pp. 519-534.
Broadwell, et al., Endocytic and exocytic pathways of the neuronal secretory process and trans-synaptic transfer of wheat germ agglutinin-horseradish peroxidase in vivo, J Comp Neurol., vol. 242, No. 4, Dec. 22, 1985, pp. 632-650.
Brooks, et al., El Escorial revisited: revised criteria for the diagnosis of amyotrophic lateral sclerosis, Amyotroph Lateral Scler Other Motor Neuron Disord., vol. 1, No. 5, Dec. 2000, pp. 293-299.
Buck, Linda B., Smell and Taste: The Chemical Senses, Principles of neural science, Kandel et al., 4th edition, 2000, pp. 625-652.
Capsoni, et al., Nerve growth factor and galantamine ameliorate early signs of neurodegeneration in anti-nerve growth factor mice, Proc Natl Acad Sci U S A., vol. 99, No. 19, Sep. 17, 2002, pp. 12432-12437.
Carlesi, et al., Strategies for clinical approach to neurodegeneration in Amyotrophic lateral sclerosis, Arch Ital Biol., vol. 149, No. 1, Mar. 2011, pp. 151-167.
Castrillo-Viguera, et al., Clinical significance in the change of decline in ALSFRS-R, Amyotroph Lateral Scler., vol. 11, No. 1-2, 2010, pp. 178-180.
Charlton, et al., Evaluation of effect of ephedrine on the transport of drugs from the nasal cavity to the systemic circulation and the central nervous system, J Drug Target, vol. 15, No. 5, Jun. 2007, pp. 370-377.
Chen, et al., Delivery of Nerve Growth Factor to the Brain via the Olfactory Pathway, J Alzheimers Dis., vol. 1, No. 1, Mar. 1998, pp. 35-44.
Chow, et al., Direct nose-brain transport of benzoylecgonine following intranasal administration in rats, J Pharm Sci., vol. 90, No. 11, Nov. 2001, pp. 1729-1735.
Chow, et al., Direct transport of cocaine from the nasal cavity to the brain following intranasal cocaine administration in rats, J Pharm Sci., vol. 88, No. 8, Aug. 1999, pp. 754-758.
Cserr, et al., Drainage of brain extracellular fluid into blood and deep cervical lymph and its immunological significance, Brain Pathol., vol. 2, No. 4, Oct. 1992, pp. 269-276.
Cserr, et al., Efflux of radiolabeled polyethylene glycols and albumin from rat brain, Am J Physiol., vol. 240, No. 4, Apr. 1981, pp. F319-F328.
Dahlin, et al., Levels of dopamine in blood and brain following nasal administration to rats, Eur J Pharm Sci., vol. 14, No. 1, Aug. 2001, pp. 75-80.
Dhuria, et al., Intranasal drug targeting of hypocretin-1 (orexin-A) to the central nervous system, J Pharm Sci., vol. 98, No. 7, Jul. 2009, pp. 2501-2515.
Dhuria, et al., Novel vasoconstrictor formulation to enhance intranasal targeting of neuropeptide therapeutics to the central nervous system, J Pharmacol Exp Ther., vol. 328, No. 1, Jan. 2009, pp. 312-320.
Diest, et al., An ultrastructural study of the endonasal microcirculation in the Wistar rat during fetal and early postnatal life, J Anat., vol. 128, No. 2, Mar. 1979, pp. 293-300.
Djupesland, et al., Breath actuated device improves delivery to target sites beyond the nasal valve, Laryngoscope, vol. 116, No. 3, Mar. 2006, pp. 466-472.
Duyao, et al., Trinucleotide repeat length instability and age of onset in Huntington's disease, Nat Genet., vol. 4, No. 4, Aug. 1993, pp. 387-392.
Field, et al., Ensheathment of the olfactory nerves in the adult rat, J Neurocytol., vol. 32, No. 3, Mar. 2003, pp. 317-324.
Fliedner, et al., Brain uptake of intranasally applied radioiodinated leptin in Wistar rats, Endocrinology, vol. 147, No. 5, May 2006, pp. 2088-2094.
Francis, et al., Intranasal insulin prevents cognitive decline, cerebral atrophy and white matter changes in murine type I diabetic encephalopathy, Brain, vol. 131, No. 12, Dec. 2008, pp. 3311-3334.
Fuss, et al., The Grueneberg ganglion of the mouse projects axons to glomeruli in the olfactory bulb, Eur J Neurosci., vol. 22, No. 10, Nov. 2005, pp. 2649-2654.
Gao, et al., UEA I-bearing nanoparticles for brain delivery following intranasal administration, Int J Pharm., vol. 340, No. 1-2, Aug. 1, 2007, pp. 207-215.
Gordon, Paul H., Amyotrophic Lateral Sclerosis: An update for 2013 Clinical Features, Pathophysiology, Management and Therapeutic Trials, Aging Dis., vol. 4, No. 5, Oct. 1, 2013, pp. 295-310.
Graff, et al., Functional evidence for P-glycoprotein at the nose-brain barrier, Pharm Res., vol. 22, No. 1, Jan. 2005, pp. 86-93.
Graff, et al., Pharmacokinetics of substrate uptake and distribution in murine brain after nasal instillation, Pharm Res., vol. 22, No. 2, Feb. 2005, pp. 235-244.
Grevers, et al., Fenestrated endothelia in vessels of the nasal mucosa. An electron-microscopic study in the rabbit, Arch Otorhinolaryngol., vol. 244, No. 1, 1987, pp. 55-60.
Groothuis, et al., Efflux of drugs and solutes from brain: the interactive roles of diffusional transcapillary transport, bulk flow and capillary transporters, J Cereb Blood Flow Metab., vol. 27, No. 1, Jan. 2007, pp. 43-56.
Hanson, et al., Intranasal administration of CNS therapeutics to awake mice, J Vis Exp., vol. 8, No. 74, Apr. 8, 2013, 7 pages.
Hanson, et al., Intranasal delivery bypasses the blood-brain barrier to target therapeutic agents to the central nervous system and treat neurodegenerative disease, BMC Neurosci., vol. 9, No. Suppl 3: S5, Dec. 10, 2008, 4 pages.
Hatterer, et al., How to drain without lymphatics? Dendritic cells migrate from the cerebrospinal fluid to the B-cell follicles of cervical lymph nodes, Blood, vol. 107, No. 2, Jan. 15, 2006, pp. 806-812.
Horowitz, S H., Ganglioside (Cronassial) therapy in diabetic neuropathy, Adv Exp Med Biol., vol. 174, 1984, pp. 593-600.
Huntington Study Group, Unified Huntington's Disease Rating Scale: reliability and consistency. Huntington Study Group, Mov Disord., vol. 11, No. 2, Mar. 1996, pp. 136-142.
International Search Report received for PCT Patent Application No. PCT/US2022/012993, mailed on Jun. 16, 2022, 7 pages.
Itaya, et al., Anterograde transsynaptic transport of WGA-HRP in the limbic system of rat and monkey, Brain Res., vol. 398, No. 2, Nov. 29, 1986, pp. 397-402.
Itokazu, et al., Epigenetic regulation of ganglioside expression in neural stem cells and neuronal cells, Glycoconj J., vol. 34, No. 6, Dec. 2017, pp. 749-756.
Itokazu, et al., Gangliosides in Nerve Cell Specification, Prog Mol Biol Transl Sci., vol. 156, 2018, pp. 241-263.
Itokazu, et al., Intracerebroventricular Infusion of Gangliosides Augments the Adult Neural Stem Cell Pool in Mouse Brain, ASN Neuro., vol. 11, No. 1-8, 2019, 8 pages.
Itokazu, et al., Intranasal infusion of GD3 and GM1 gangliosides downregulates alpha-synuclein and controls tyrosine hydroxylase gene in a PD model mouse, Mol Ther., vol. 29, No. 10, Oct. 6, 2021, pp. 3059-3071.
Jankovic , J., Parkinson's disease: clinical features and diagnosis, J Neurol Neurosurg Psychiatry, vol. 79, No. 4, Apr. 2008, pp. 368-376.
Jansson, et al., Visualization of in vivo olfactory uptake and transfer using fluorescein dextran, J Drug Target., vol. 10, No. 5, Aug. 2002, pp. 379-386.
Johnston, et al., Evidence of connections between cerebrospinal fluid and nasal lymphatic vessels in humans, non-human primates and other mammalian species, Cerebrospinal Fluid Res., vol. 1, No. 2, Dec. 10, 2004, 13 pages.
Karpiak, S E., Exogenous gangliosides enhance recovery from cns injury, Adv Exp Med Biol., vol. 174, 1984, pp. 489-497.
Kida, et al., CSF drains directly from the subarachnoid space into nasal lymphatics in the rat. Anatomy, histology and immunological significance, Neuropathol Appl Neurobiol., vol. 19, No. 6, Dec. 1993, pp. 480-488.
Koos, et al., The Grueneberg ganglion projects to the olfactory bulb, Neuroreport., vol. 16, No. 17, Nov. 28, 2005, pp. 1929-1932.

(56) References Cited

OTHER PUBLICATIONS

Kristensson, et al., Uptake of exogenous proteins in mouse olfactory cells, Acta Neuropathol., vol. 19, No. 2, 1971, pp. 145-154.
Kumar, et al., Uptake of Radioactivity by Body Fluids and Tissues in Rhesus Monkeys After Intravenous Injection or Intranasal Spray of Tritium-Labelled Oestradiol and Progesterone, Current Science, vol. 43, No. 14, Jul. 20, 1974, pp. 435-439.
Ledeen, et al., Gangliosides: structure, isolation, and analysis, Methods Enzymol., vol. 83, 1982, pp. 139-191.
Li, et al., Interaction of olfactory ensheathing cells with astrocytes may be the key to repair of tract injuries in the spinal cord: the 'pathway hypothesis', J Neurocytol., vol. 34, No. 3-5, Sep. 2005, pp. 343-351.
Li, et al., Olfactory ensheathing cells and olfactory nerve fibroblasts maintain continuous open channels for regrowth of olfactory nerve fibres, Glia, vol. 52, No. 3, Nov. 15, 2005, pp. 245-251.
Lorenzo, A.J. Darin De, The Olfactory Neuron and the Blood-brain Barrier, Taste And Smell in Vertebrates, Edited by Wolstenholme et al., 1970, pp. 151-176.
Luzzati, et al., X-ray scattering study of pike olfactory nerve: elastic, thermodynamic and physiological properties of the axonal membrane, J Mol Biol., vol. 343, No. 1, Oct. 8, 2004, pp. 199-212.
Macijauskienė, et al., Dementia with Lewy bodies: the principles of diagnostics, treatment, and management, Medicina (Kaunas), vol. 48, No. 1, 2012, pp. 1-8.
Mackenzie, et al., TDP-43 and FUS in amyotrophic lateral sclerosis and frontotemporal dementia, Lancet Neurol., vol. 9, No. 10, Oct. 2010, pp. 995-1007.
Mahadik, et al., Gangliosides in treatment of neural injury and disease, Drug Development Research, vol. 15, No. 4, 1988, pp. 337-360.
Marshall, et al., Specific psychiatric manifestations among preclinical Huntington disease mutation carriers, Arch Neurol., vol. 64, No. 1, Jan. 2007, pp. 116-121.
Martinez, et al., Intranasal delivery of insulin and a nitric oxide synthase inhibitor in an experimental model of amyotrophic lateral sclerosis, Neuroscience, vol. 157, No. 4, Dec. 10, 2008, pp. 908-925.
Mu, et al., Adult hippocampal neurogenesis and its role in Alzheimer's disease, Mol Neurodegener., vol. 6, No. 85, Dec. 22, 2011, 9 pages.
Nakatani, et al., Characterization of GD3 ganglioside as a novel biomarker of mouse neural stem cells, Glycobiology., vol. 20, No. 1, Jan. 2010, pp. 78-86.
Nonaka, et al., Delivery of galanin-like peptide to the brain: targeting with intranasal delivery and cyclodextrins, J Pharmacol Exp Ther., vol. 325, No. 2, May 2008, pp. 513-519.
Pardridge, William M., The blood-brain barrier: bottleneck in brain drug development, NeuroRx., vol. 2, No. 1, Jan. 2005, pp. 3-14.
Perl, et al., Uptake of aluminium into central nervous system along nasal-olfactory pathways, Lancet, vol. 1, No. 8540, May 2, 1987, p. 1028.
Pollock, et al., Perivascular spaces in the basal ganglia of the human brain: their relationship to lacunes, J Anat., vol. 191, No. 3, Oct. 1997, pp. 337-346.
Ren, et al., O-acetylated gangliosides in bovine buttermilk. Characterization of 7-O-acetyl, 9-O-acetyl, and 7,9-di-O-acetyl GD3, J Biol Chem., vol. 267, No. 18, Jun. 25, 1992, pp. 12632-12638.
Rennels, et al., Evidence for a 'paravascular' fluid circulation in the mammalian central nervous system, provided by the rapid distribution of tracer protein throughout the brain from the subarachnoid space, Brain Res., vol. 326, No. 1, Feb. 4, 1985, pp. 47-63.
Rosenberg, et al., Neuropsychological characteristics of Huntington's disease carriers: a double blind study, J Med Genet., vol. 32, No. 8, Aug. 1995, pp. 600-604.
Ross, et al., Intranasal administration delivers peptoids to the rat central nervous system, Neurosci Lett., vol. 439, No. 1, Jul. 4, 2008, pp. 30-33.
Ross, et al., Intranasal administration of interferon beta bypasses the blood-brain barrier to target the central nervous system and cervical lymph nodes: a non-invasive treatment strategy for multiple sclerosis, J Neuroimmunol., vol. 151, No. 1-2, Jun. 2004, pp. 66-77.
Rowland, et al., Amyotrophic lateral sclerosis, N Engl J Med., vol. 344, No. 22, May 31, 2001, pp. 1688-1700.
Sakane, et al., Direct drug transport from the rat nasal cavity to the cerebrospinal fluid: the relation to the dissociation of the drug, J Pharm Pharmacol., vol. 46, No. 5, May 1994, pp. 378-379.
Sakane, et al., Direct drug transport from the rat nasal cavity to the cerebrospinal fluid: the relation to the molecular weight of drugs, J Pharm Pharmacol., vol. 47, No. 5, May 1995, pp. 379-381.
Schaefer, et al., Trigeminal collaterals in the nasal epithelium and olfactory bulb: a potential route for direct modulation of olfactory information by trigeminal stimuli, J Comp Neurol., vol. 444, No. 3, Mar. 12, 2002, pp. 221-226.
Scheibe, et al., Intranasal administration of drugs, Arch Otolaryngol Head Neck Surg., vol. 134, No. 6, Jun. 2008, pp. 643-646.
Shipley, M. T., Transport of molecules from nose to brain: transneuronal anterograde and retrograde labeling in the rat olfactory system by wheat germ agglutinin-horseradish peroxidase applied to the nasal epithelium, Brain Res Bull., vol. 15, No. 2, Aug. 15, 1985, pp. 129-143.
Shiwach, R., Psychopathology in Huntington's disease patients, Acta Psychiatr Scand., vol. 90, No. 4, Oct. 1994, pp. 241-246.
Sleiman, et al., Exercise promotes the expression of brain derived neurotrophic factor (BDNF) through the action of the ketone body β-hydroxybutyrate, Elife, vol. 5, Jun. 2, 2016, 21 pages.
Smulders, et al., Reproductive options for prospective parents in families with Huntington's disease: clinical, psychological and ethical reflections, Hum Reprod Update., vol. 19, No. 3, Feb. 1, 2013, pp. 304-315.
Tang, et al., Ganglioside GD3 regulates dendritic growth in newborn neurons in adult mouse hippocampus via modulation of mitochondrial dynamics, J Neurochem., vol. 156, No. 6, Mar. 2021, pp. 819-833.
Thorne, et al., Delivery of insulin-like growth factor-I to the rat brain and spinal cord along olfactory and trigeminal pathways following intranasal administration, Neuroscience, vol. 127, No. 2, 2004, pp. 481-496.
Thorne, et al., Delivery of interferon-beta to the monkey nervous system following intranasal administration, Neuroscience, vol. 152, No. 3, Mar. 27, 2008, pp. 785-797.
Thorne, et al., Delivery of neurotrophic factors to the central nervous system: pharmacokinetic considerations, Clin Pharmacokinet., vol. 40, No. 12, 2001, pp. 907-946.
Thorne, et al., Quantitative analysis of the olfactory pathway for drug delivery to the brain, Brain Res., vol. 692, No. (1-2), Sep. 18, 1995, pp. 278-282.
Tsai, et al., Epigenetic activation of mouse ganglioside synthase genes: implications for neurogenesis, J Neurochem., vol. 128, No. 1, Jan. 2014, pp. 101-110.
Tsai, et al., GM1 Ganglioside is Involved in Epigenetic Activation Loci of Neuronal Cells, Neurochem Res., vol. 41, No. 1-2, Feb. 1, 2016, pp. 107-115.
Videnovic, et al., Circadian Melatonin Rhythm and Excessive Daytime Sleepiness in Parkinson Disease, JAMA Neurol., vol. 71, No. 4, Feb. 24, 2014, pp. 463-469.
Vyas, et al., Intranasal mucoadhesive microemulsions of clonazepam: preliminary studies on brain targeting, J Pharm Sci., vol. 95, No. 3, Mar. 2006, pp. 570-580.
Waldemar, et al., Recommendations for the diagnosis and management of Alzheimer's disease and other disorders associated with dementia: EFNS guideline, Eur J Neurol., vol. 14, No. 1, Jan. 2007, pp. e1-e6.
Walker, Francis O., Huntington's disease, Lancet, vol. 369, No. 9557, Jan. 20, 2007, pp. 218-228.
Walter, et al., Evidence of antibody production in the rat cervical lymph nodes after antigen administration into the cerebrospinal fluid, Arch Histol Cytol., vol. 69, No. 1, Mar. 2006, pp. 37-47.
Walter, et al., The olfactory route for cerebrospinal fluid drainage into the peripheral lymphatic system, Neuropathol Appl Neurobiol., vol. 32, No. 4, Aug. 2006, pp. 388-396.

(56) References Cited

OTHER PUBLICATIONS

Wang, et al., Ganglioside GD3 is required for neurogenesis and long-term maintenance of neural stem cells in the postnatal mouse brain, J Neurosci., vol. 34, No. 41, Oct. 8, 2014, pp. 13790-13800.
Wang, et al., Interaction of ganglioside GD3 with an EGF receptor sustains the self-renewal ability of mouse neural stem cells in vitro, Proc Natl Acad Sci U S A., vol. 110, No. 47, Nov. 19, 2013, pp. 19137-19142.
Wang, et al., Pharmacokinetics of Gastrodin in rat plasma and CSF after i.n. and i.v, Int J Pharm., vol. 341, No. (1-2), Aug. 16, 2007, pp. 20-25.
Wang, et al., The melatonin MT1 receptor axis modulates mutant Huntingtin-mediated toxicity, J Neurosci., vol. 31, No. 4, Oct. 12, 2011, pp. 14496-14507.
Williams, et al., Response of olfactory ensheathing cells to the degeneration and regeneration of the peripheral olfactory system and the involvement of the neuregulins, J Comp Neurol., vol. 470, No. 1, Feb. 23, 2004, pp. 50-62.
Yu, et al., Functional roles of gangliosides in neurodevelopment: an overview of recent advances, Neurochem Res., vol. 37, No. 6, Jun. 2012, pp. 1230-1244.
Yu, et al., Glycolipid and glycoprotein expression during neural development, Adv Neurobiol., vol. 9, 2014, pp. 185-222.

* cited by examiner

Intensity of nuclear Nurr1

*

*

1

0.5

0

Saline

Saline

GD3

GM1

GD3/GM1

WT

PD

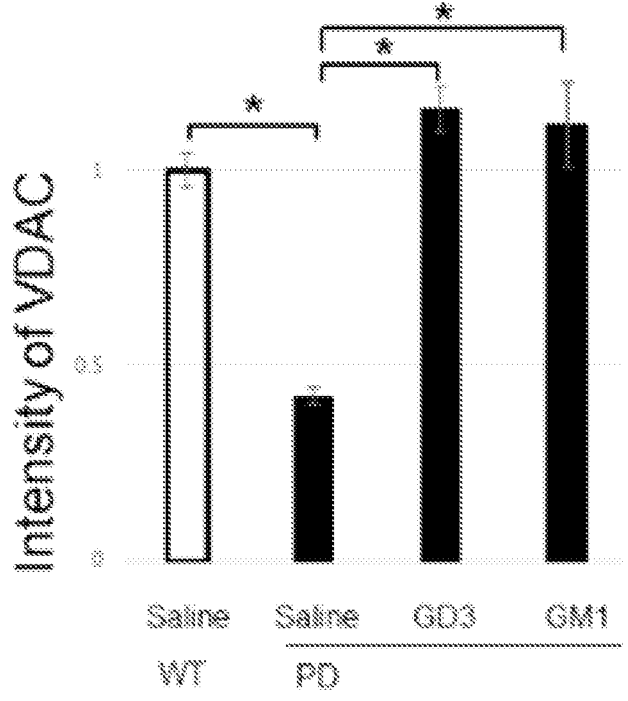
FIG. 6
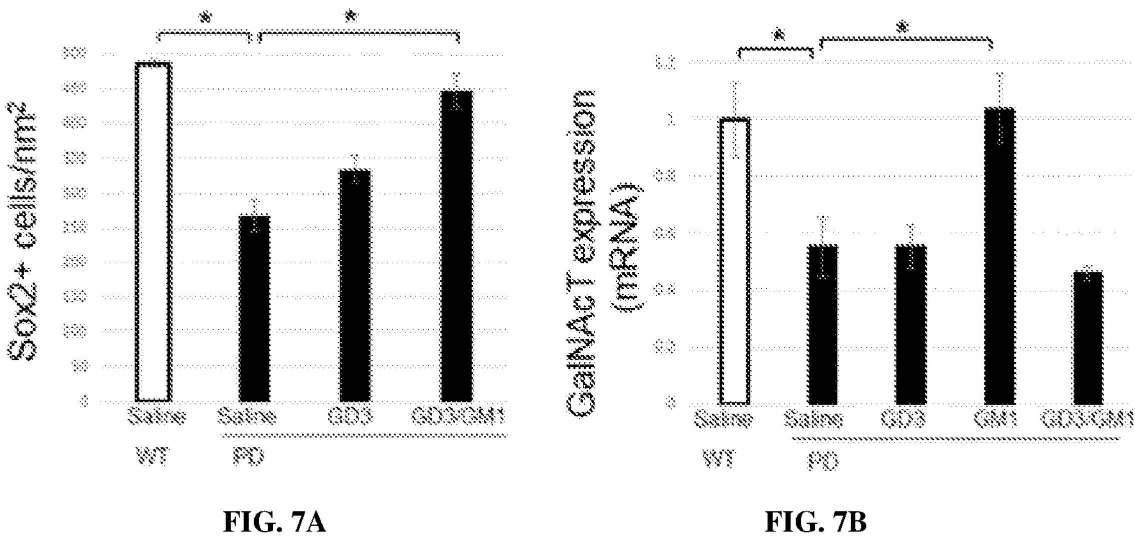
FIG. 7A
FIG. 7B

```
SEQUENCE LISTING

<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 1

cactatgccc acccccag                                               18


<210> SEQ ID NO 2
<211> LENGTH: 18
<212> TYPE: DNA
<213> ORGANISM: Artificial Sequence
<220> FEATURE:
<223> OTHER INFORMATION: synthetic polynucleotide

<400> SEQUENCE: 2

cgccgtccaa tgaacctt                                               18


<210> SEQ ID NO 3
<211> LENGTH: 22
<212> TYPE: DNA
<213> ORGANISM: Artificial Sequence
<220> FEATURE:
<223> OTHER INFORMATION: synthetic polynucleotide

<400> SEQUENCE: 3

ctaaggccaa ccgtgaaaag at                                          22


<210> SEQ ID NO 4
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 4

cacagcctgg atggctacgt                                             20


<210> SEQ ID NO 5
<211> LENGTH: 20
<212> TYPE: DNA
```

<213> ORGANISM: Artificial Sequence
<220> FEATURE:
<223> OTHER INFORMATION: synthetic polynucleotide

<400> SEQUENCE: 5
taagaggccg cctgcctggc 20

<210> SEQ ID NO 6
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 6
gtctcgtcct atggttcgtc 20

<210> SEQ ID NO 7
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 7
tccaggagaa cagacgccag c 21

<210> SEQ ID NO 8
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 8
gccaggctga aggcaagcac a 21

<210> SEQ ID NO 9
<211> LENGTH: 21
<212> TYPE: DNA
<213> ORGANISM: Artificial Sequence
<220> FEATURE:
<223> OTHER INFORMATION: synthetic polynucleotide

<400> SEQUENCE: 9
ttccatgaaa gcacaactgg c 21

<210> SEQ ID NO 10
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 10
cagggtcggc tgctgaggat 20

<210> SEQ ID NO 11
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 11
accagggagg gctgcagtcc 20

-continued

```
<210> SEQ ID NO 12
<211> LENGTH: 20
<212> TYPE: DNA
<213> ORGANISM: Artificial Sequence
<220> FEATURE:
<223> OTHER INFORMATION: synthetic polynucleotide

<400> SEQUENCE: 12

tcagttcgga gcccacacgc                                    20
```

METHODS AND COMPOSITIONS FOR TREATING NEURODEGENERATIVE DISEASES

CROSS-REFERENCE TO RELATED APPLICATION

This application is a National Phase application under U.S.C. § 371 of PCT/US2022/012993, filed Jan. 19, 2022, which claims the benefit of and priority to U.S. Ser. No. 63/139,057 filed Jan. 19, 2021, and which are incorporated by reference herein in their entireties.

STATEMENT REGARDING FEDERALLY SPONSORED RESEARCH OR DEVELOPMENT

This invention was made with Government support under NS100839 awarded by the National Institutes of Health. The Government has certain rights in the invention.

REFERENCE TO THE SEQUENCE LISTING

The Sequence Listing submitted as a text file named "AURI_2021_012_PCT_ST25" created on Jan. 19, 2022 and having a size of 2,680 bytes is hereby incorporated by reference pursuant to 37 C.F.R. § 1.52(e)(5).

FIELD OF THE INVENTION

The invention is generally directed to methods and compositions for treating neurodegenerative diseases.

BACKGROUND OF THE INVENTION

Neurological diseases are generally characterized by neuronal loss in one or more regions of the central nervous system. Examples of neurological diseases include Alzheimer's disease, neurofibromatosis, Huntington's disease, depression, amyotrophic lateral sclerosis, multiple sclerosis, stroke, Parkinson's disease and multiple infarction dementia. These diseases are complex in both origin and progression and have proven to be some of the most difficult disease types to treat. In fact, there are no effective drugs that provide substantial therapeutic benefit for some neurological diseases. Given the adverse effects these diseases have on victims, the difficulty of providing treatment is even more tragic.

Alzheimer's disease (AD) is a degenerative brain disease characterized by clinically progressive progression of memory, cognition, reasoning, judgment, and emotional stability, which gradually leads to severe mental devastation and eventually death. AD is the most common cause of progressive mental disorder (dementia) in older people and the fourth most common cause of medical death in the United States. AD has been observed in all ethnic and ethnic groups worldwide and appears as a major public health problem now and in the future. The disease is currently estimated to affect about 4 million people in the United States alone. AD is currently incurable. Administration of certain therapeutic agents has been used to treat the symptoms of AD in humans. However, therapies that effectively prevent AD or restore its symptoms or progression in humans are currently unknown.

Alzheimer's disease is characterized by the accumulation of a 39-43 amino acid peptide termed the β-amyloid protein or Aβ, in a fibrillar form, existing as extracellular amyloid plaques and as amyloid within the walls of cerebral blood vessels. Fibrillar Aβ amyloid deposition in Alzheimer's disease is believed to be detrimental to the patient and eventually leads to toxicity and neuronal cell death, characteristic hallmarks of Alzheimer's disease. Accumulating evidence implicates amyloid, and more specifically, the formation, deposition, accumulation and/or persistence of Aβ fibrils, as a major causative factor of Alzheimer's disease pathogenesis. In addition, besides Alzheimer's disease, a number of other amyloid diseases involve formation, deposition, accumulation and persistence of Aβ fibrils, including Down's syndrome, disorders involving congophilic angiopathy, such as but not limited to, hereditary cerebral hemorrhage of the Dutch type, inclusion body myositis, dementia pugilistica, cerebral β-amyloid angiopathy, dementia associated with progressive supranuclear palsy, dementia associated with cortical basal degeneration and mild cognitive impairment.

Parkinson's disease (PD) is another human disorder characterized by the formation, deposition, accumulation and/or persistence of abnormal fibrillar protein deposits that demonstrate many of the characteristics of amyloid. In Parkinson's disease, an accumulation of cytoplasmic Lewy bodies consisting of filaments of α-synuclein/NAC (non-Aβ component) are believed important in the pathogenesis and as therapeutic targets. New agents or compounds able to inhibit α-synuclein and/or NAC formation, deposition, accumulation and/or persistence, or disrupt pre-formed α-synuclein/NAC fibrils (or portions thereof) are regarded as potential therapeutics for the treatment of Parkinson's and related synucleinopathies. NAC is a 35 amino acid fragment of α-synuclein that has the ability to form amyloid-like fibrils either in vitro or as observed in the brains of patients with Parkinson's disease. The NAC fragment of α-synuclein is a relative important therapeutic target as this portion of α-synuclein is believed crucial for formation of Lewy bodies as observed in all patients with Parkinson's disease, synucleinopathies and related disorders.

Thus, it is an object of the invention to provide effective and less invasive methods and compositions for treating neurodegenerative diseases.

SUMMARY OF THE INVENTION

Methods and compositions for treating neurodegenerative diseases are provided herein. In some embodiments, the methods feature intranasal delivery of gangliosides to the central nervous system (CNS) to prevent, inhibit or treat neurodegenerative diseases. As described herein, intranasally administrated gangliosides were delivered to brain tissue including olfactory bulb, hippocampus, midbrain, cortex, and cerebellum. Intranasal infusion of gangliosides removed cytotoxic proteins and restored NSC activities in PD mice. The results thus demonstrate that exogenously administered gangliosides, specifically GD3 and GM1, are capable of restoring the function of postnatal NSCs. GD3 restores NSC self-renewal to prevent progression of neurodegeneration, GM1 enhances neuronal differentiation to prevent progression of neurodegeneration, GM1 removes neurotoxic proteins Aβs and aSyn, and GD3 and GM1 work greater than additively to restore adult neurogenesis and increase resiliency to neurodegeneration. As ganglioside expression profiles were shown to be associated with pathogenic mechanisms of neurodegenerative diseases, the administration of exogenous gangliosides, such as GD3 and/or GM1, presents an effective strategy for promoting adult neurogenesis in damaged CNS/brain for disease treatment. Thus, the use of gangliosides (GD3 and GM1) alone or in combination to promote neurogenesis allows for the treatment of many different neurologic disorders, including neurodegenerative diseases such as Parkinson's disease and Alzheimer's disease, and the like.

In other embodiments, gangliosides are delivered to a mammal intrathecally (IT), endovascularly (IV), cerebroventricularly (ICV), intranasally (IN), or intraocularly to prevent, inhibit or treat neurodegenerative disease, disorder, or injury.

In some embodiments, the diseases to be prevented, inhibited or treated with gangliosides include, but are not limited to, diseases related to neurologic disorders including but not limited to Huntington's disease (HD), Alzheimer's disease (AD), Parkinson's disease (PD), amyotrophic lateral sclerosis (ALS), stroke, multiple sclerosis, epilepsy, brain and eye injuries, olfactory dysfunction, and mental disorders including schizophrenia.

Thus, methods of preventing, inhibiting, and/or treating, for example one or more symptoms associated with, a disease of the CNS in a mammal in need thereof are described. The methods can include delivering to the CNS of a mammal in need of treatment a composition comprising an effective amount of gangliosides GD3 and/or GM1. The methods can include administering to the CNS of a mammal in need of treatment an effective amount of a pharmaceutical composition having a GM1 gangliosides. The methods can include administering to the CNS of a mammal in need of treatment an effective amount of a pharmaceutical composition having GD3 gangliosides. The method can involve administering the CNS of a mammal in need of treatment an effective amount of a pharmaceutical composition having a combination of GM1 and GD3 gangliosides. Diseases that may be prevented, inhibited or treated using the methods disclosed herein include, but are not limited to, Alzheimer's disease and Parkinson's disease as well as the disorders, disorders, and injuries listed herein. The gangliosides can be administered in a variety of ways to ensure delivery to the CNS/brain. Routes of delivery to the CNS/brain include, but are not limited to intrathecal administration, intracranial administration, e.g., intracerebroventricular administration, or lateral cerebroventricular administration, intranasal administration, ocular, endovascular administration, and intraparenchymal administration. The compositions can be administered two or more times. The GD3 and GM1 can administered concurrently (e.g., in the same or different admixtures), sequentially and overlapping, or sequentially and non-overlapping. In some embodiments, GD3 is administered one or more times to amplify neural stem cells prior to administering GM1 one or more times to increase differentiation of neural cells, most particularly neural stems cells including, but not limited to, those amplified by GD3.

In preferred embodiments, the methods include administering intranasally to, or into the eye of, a mammal a composition including an effective amount of gangliosides, GM1 and/or GD3, the expression of which in the central nervous system of the mammal prevents, inhibits or treats neurodegenerative diseases, disorders, or injuries.

BRIEF DESCRIPTION OF THE DRAWINGS

FIGS. 4A and 4B are graphs showing quantitation of aSyn and phospho-aSyn (S129) levels, respectively, by image analysis. FIG. 4C is a Western blot analysis of aSyn and pS129-aSyn in the substantia nigra. Values were normalized to control levels and are means±SE (n=3 mice/group Values were normalized to control levels and are means±SE. (n=3 mice/group; two-way ANOVA with a Tukey's multiple comparisons test). $*p<0.05$.

FIG. 5A shows quantitation of TH levels by image analysis. FIG. 5B shows nuclear localization of Nurr1 quantified by image analysis. Values were normalized to control levels and are means±SE. (n=3 mice/group; two-way ANOVA with a Tukey's multiple comparisons test). *p<0.05.

FIG. 6 shows intranasally administrated GD3 and GM1 restored expression of VDAC1, a major component of the outer mitochondrial membrane known to regulate mitochondrial functions. Intranasal injected GD3 or GM1 (5 mg/kg/day for 28 days) increased VDAC1 expression in PD mouse brain. FIG. 6 is a bar graph showing quantitation of VDAC levels by image analysis. Values were normalized to control levels and are means±SE. (n=3 mice/group; two-way ANOVA with a Tukey's multiple comparisons test). *p<0.05.

FIGS. 7A and 7B are bar graphs showing GD3 ganglioside restores NSC numbers and GM1 activated GM2S gene expression in PD brain. FIG. 7A shows intranasal injected GD3 (5 mg/kg/day for 28 days) augmented SOX2 positive NSCs in hippocampus of PD mouse brains. FIG. 7B shows intranasal GM1 (5 mg/kg/day for 28 days) promoted expression of GM2S for neuronal differentiation. (n=3 mice/group; two-way ANOVA with a Tukey's multiple comparisons test). *p<0.05.

FIG. 8A shows reduced TH expression in substantia nigra of GM2S-KO mouse (8 months old), and intranasal GM1 administration (5 mg/kg/day for 28 days) restored TH levels. Neuro 2a cells were cultured in the presence of gangliosides (5 mM of GM1 or GD3) for 24 h. FIG. 8B shows mRNA analysis for TH expression. FIG. 8C-8E show enrichment of epigenetic markers and recruitment of transcription factors in the TH gene promoter were analyzed by ChIP assays with anti-AcH3 (8C), anti-Nurr1 (8D), or anti-Pitx3 (8E), followed by qPCR analyses.

FIG. 9A is a schematic diagram showing the experimental procedure of novel object recognition test. FIG. 9B is a bar graph showing intranasal GD3 or GM1 (for 8 weeks), or combinational injection of GD3 and GM1 (GD3 or GM1 for 4 weeks in order) increased memory function of 5XFAD mice. Each mouse was placed in an arena, with two identical objects placed at each end of the arena. After 5 min of investigation, mice were returned to their home cage. 24 hours later, one test object was replaced with a novel object, and animals were allowed 5 min for investigation. The time spent exploring each object was recorded. Percentages of exploration time of novel object (memory) are shown in the columns (n=3).

FIG. 10A is an illustration of the buried pellet test used to measure olfactory function. FIG. 10B is a bar graph showing intranasal GM1 (for 8 weeks), or combinational injection of GD3 and GM1 (GD3 or GM1 for 4 weeks in order) enhanced olfactory function of 5XFAD mice. (n=3).

FIG. 11A-11C are bar graphs showing intranasal GD3 or GM1 (for 8 weeks), or combinational injection of GD3 and GM1 (GD3 or GM1 for 4 weeks in order) increased bone area (11A), bone mineral density (11B), and bone mineral content (11C) of 5XFAD mice. (n=3)

DETAILED DESCRIPTION OF THE INVENTION

I. Definitions

Figure 1A:
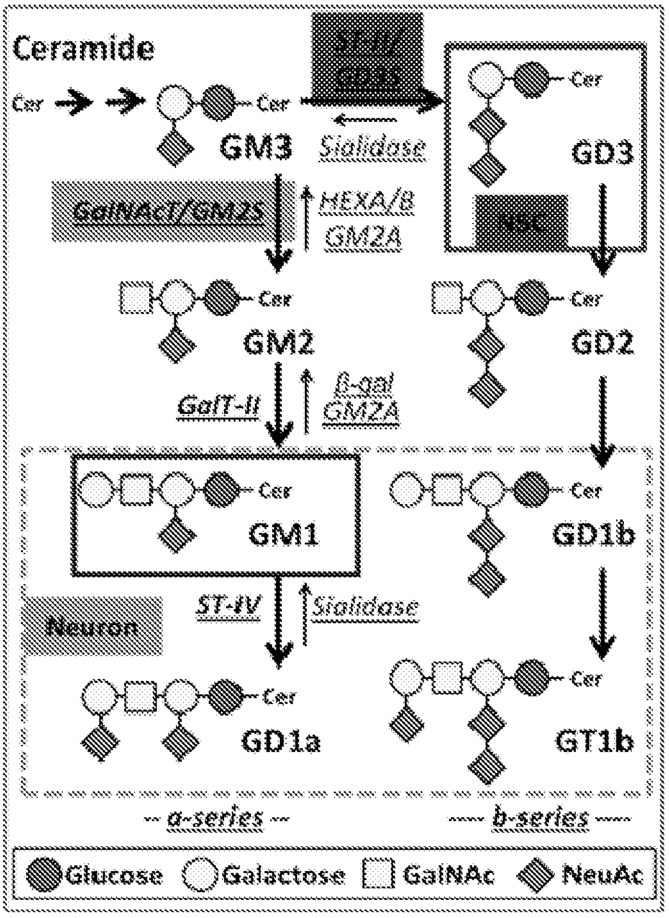
FIG. 1A is an image displaying the structure and metabolic pathways of gangliosides. It demonstrates the reaction pathway to synthesize both GM1 and GD3 as well as further reaction pathways that can occur after synthesis.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other embodiments the values may range in value either above or below the stated value in a range of approx. +/−5%; in other embodiments the values may range in value either above or below the stated value in a range of approx. +/−2%; in other embodiments the values may range in value either above or below the stated value in a range of approx. +/−1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treatment" and "treating", as used herein, refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

The term "individual," "host," "subject," and "patient" are used interchangeably to refer to any individual who is the target of administration or treatment. The subject can be a vertebrate, for example, a mammal Thus, the subject can be a human or veterinary patient.

The term "therapeutically effective" means that the amount of the composition used is of sufficient quantity to ameliorate one or more causes or symptoms of a disease or disorder. Such amelioration only requires a reduction or alteration, not necessarily elimination. A therapeutically effective amount of a composition for treating cancer is preferably an amount sufficient to cause tumor regression or to sensitize a tumor to radiation or chemotherapy.

The term "pharmaceutically acceptable" refers to a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

II. Methods for Treating Neurodegenerative Diseases

Patients with Alzheimer's disease (AD), Parkinson's disease (PD), Strokes, Huntington's disease (HD), amyotrophic lateral sclerosis (ALS), and multiple sclerosis (MS), and other neurodegenerative diseases suffer from disease progression without any satisfying clinical intervention. Gangliosides are important in mediating neurotrophic and other vital functions necessary for long-term maintenance of neuronal viability. A large majority of cases of neurodegenerative disorders show significant deficiency of gangliosides in the brain. The disclosed compositions and methods can be used inhibit disease development by removing neurotoxic proteins (Aβs and aSyn), and in the meantime, by restoring neurogenesis in brains.

Remarkably, gangliosides GM1 (also referred to as monosialotetrahexosylganglioside), GD3 (also referred to as monosialodihexosylganglioside) (FIGS. 1A, and 1B) and others are capable of forming complexes with Aβs or aSyn. Gangliosides play an important functional role in neural stem cells (NSCs), such as proliferation, differentiation, migration, and signal transduction. Results show that ganglioside composition changes dramatically during brain development and neuronal differentiation. GD3 is the most abundant species in NSCs (>80%) (Nakatani et al., *Glycobiology,* 20(1):78-86 (2010)), and its synthesis is switched into the synthesis of more complex gangliosides during development, resulting in terminal differentiation and loss of the "stemness" of NSCs. Further alterations of ganglioside expression in AD and PD patients have been reported. The disclosed compositions and methods provide a means to reduce the toxic form of Aβs and aSyn by neuroprotective gangliosides, to delay or even prevent disease progression, and to increase the resilience of brains by promoting adult neurogenesis by gangliosides (GD3 & GM1).

Activation of adult neurogenesis is promoted by neurotrophic factors whose signaling is dependent on their lipid environment. For example, GD3 ganglioside modulates NSC self-renewal by interacting with EGF receptors and regulating EGF signaling, and GM1 ganglioside is necessary for the formation of the GDNF-receptor complex in dopaminergic neurons. Moreover, results show that GM1 augments epigenetic gene regulation mechanism for neuronal cell lineage differentiation. Rescue experiments by intracerebroventricular (icv) infusion of ganglioside GD3 in adult GD3 synthase (GD3S)-KO animals show that it could restore the NSC pools and enhance the NSCs for self-renewal. Further, 5xFAD mouse model was utilized, and GD3 restored NSC numbers and GM1 promoted neuronal differentiation. These results show that exogenously administered gangliosides are capable of restoring the function of postnatal NSCs.

However, subcutaneous or intramuscular injection of ganglioside of GM1 alone to treat central nervous system disorders has been tried with inconsistent outcome. Gangliosides form micelles and are normally not permeable through the blood-brain barrier. So far, icv administration is the most reliable method to deliver gangliosides into the brain, not a preferred method for treating human patients.

The disclosed methods can utilize a more convenient, non-invasive delivery procedure by intranasal infusion of gangliosides. The experiments in the Examples below illustrate that intranasally administrated gangliosides were delivered to brain tissue including olfactory bulb, hippocampus, midbrain, cortex, and cerebellum. Intranasal infusion of gangliosides removed cytotoxic proteins and restored NSC activities in PD mice.

Figure 2A:
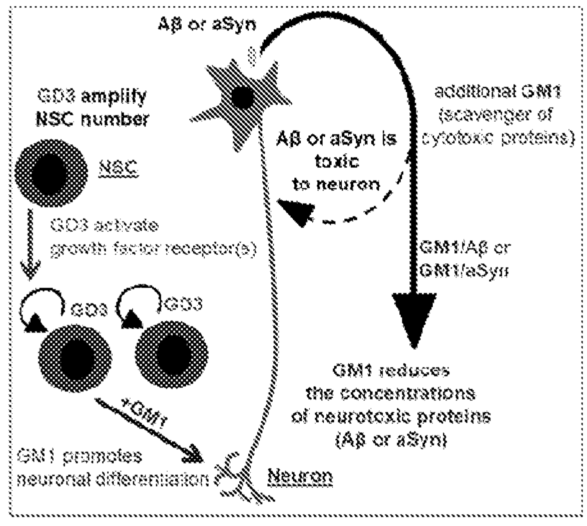
FIG. 2A is a schematic diagram displaying the effect of GD3 and GM1 on neural stem cells (NSC). While GD3 amplifies the number of NSCs, GM1 promotes the differentiation of NSCs and removes harmful cytotoxins (e.g. Aβ or aSyn).

More particularly, the results presented below show that intranasal infusion of GM1 reduced aSyn levels and significantly enhanced expression of tyrosine hydroxylase (TH) in the substantia nigra pars compacta (SNpc) of A53T aSyn overexpressing mouse (PD mouse). GM1 restored nuclear expression of Nurr1, an important transcription factor for differentiation, maturation, and maintenance of midbrain dopaminergic neurons. Further administration of GD3 augments self-renewal and multipotent marker, SOX2-expressing cells at hippocampus and GM1 increases the expression of GM2 synthase (GM2S) to promote neuronal differentiation in a PD model mouse. Since ganglioside expression profiles are associated with pathogenic mechanisms of neurodegenerative diseases, such as AD, PD, Huntington's disease (HD), amyotrophic lateral sclerosis (ALS), and multiple sclerosis (MS), the disclosed compositions and methods of administering exogenous gangliosides, such as GD3 and GM1, are believed to be an effective strategy for eliminating toxic proteins and for promoting adult neurogenesis in damaged brain for disease treatment (FIG. 2A).

The disclosed composition and methods relate to the treatment of neurodegenerative diseases, disorders, and/or conditions, with gangliosides GM1 and/or GD3. Methods and compositions for application are provided. In preferred embodiments, the disclosed compositions and methods activate neurogenesis in an individual diagnosed with, or at risk of having, or suspected of having a neurodegenerative disease, disorder, and/or condition. Methods of administering a therapeutic agent are provided. In particular, provided are methods of administering gangliosides GM1 and GD3 to the central nervous system (CNS) for the removal of cytotoxic proteins and restoring neural stem cells activity to prevent, inhibit or treat neurodegenerative diseases. Specifically, in some aspects, the disclosure provides methods of intranasal delivery of gangliosides GM1 and GD3 to the CNS, thereby providing effective treatment and/or prevention of neurodegenerative diseases.

A. Compositions

1. Gangliosides

The disclosed methods typically include administering a subject in need thereof GD3 and/or GM1 ganglioside. Gangliosides are a class of three-component glycolipids that are often found in cell membranes. One or more sialic acid residues are attached to the oligosaccharide or carbohydrate core moiety. This sialic acid residue is then bound to a hydrophobic lipid (ceramide) structure, which is generally embedded in the cell membrane. The ceramide moiety includes a long chain base (LCB) moiety and a fatty acid (FA) moiety. Gangliosides and other glycolipids and their structures are generally described, for example, by Lehninger, Biochemistry (Worth Publishers, 1981) 287-295 and Devlin, Text. book of Biochemistry (Wiley-Liss, 1992).

Gangliosides are most abundant in the brain, particularly in the nerve endings. They are thought to exist at receptor sites for neurotransmitters, including acetylcholine, and also act as specific receptors for other biopolymers, including interferons, hormones, viruses, bacterial toxins, etc. obtain. Gangliosides are used for the treatment of nervous system disorders. For example, Mahadnik et al. (1988) *Drug Development Res.* 15337-360; U.S. Pat. No. 4,710,490; Horowitz (1988) *Adv. Exp. Med. and Biol.* 174: 593-600; Karpiatz et al. (1984) *Adv. Exp. Med. and Biol.* 174: 489-497, all of which are incorporated by reference.

Gangliosides are active in modulating oligomerization and aggregation of cytotoxic proteins, including amyloid β-peptide (Aβ) and alpha-synuclein (aSyn), that are the major pathologic hallmarks of cell death in AD and PD. It is believed that deficiency of GM1 ganglioside is a contributor to AD and PD pathogenesis. Gangliosides are important in mediating neurotrophic and other vital functions need for long-term maintenance of neuronal viability. A large majority of cases of neurodegenerative disorders show significant deficiency of gangliosides in the brain.

Gangliosides GM1, GD3 (see e.g., FIGS. 1A and 1B) and others are capable of forming complexes with Aβs or aSyn. Gangliosides play an important functional role in neural stem cells (NSCs), such as proliferation, differentiation, migration, and signal transduction. It is thought that ganglioside composition changes dramatically during brain development and neuronal differentiation. GD3 has been found to be the most abundant species in NSCs (>80%), and its synthesis is switched into the synthesis of more complex gangliosides during development, resulting in terminal differentiation and loss of the "sternness" of NSCs. Further alterations of ganglioside expression in AD and PD patients have been reported.

Because ganglioside expression profiles are associated with pathogenic mechanisms of neurodegenerative diseases, such as AD, PD, Huntington's disease (HD), amyotrophic lateral sclerosis (ALS), and multiple sclerosis (MS), it is believed that administration of exogenous gangliosides, such as GD3 and GM1, may represent an effective strategy for eliminating toxic proteins and for promoting adult neurogenesis in damaged brain for disease treatment. Stimulation and use of endogenous NSCs is believed to be safer alternative to stem cell therapy.

Activation of adult neurogenesis is known to be promoted by neurotrophic factors whose signaling is dependent on their lipid environment. For example, GD3 ganglioside modulates NSC self-renewal by interacting with EGF receptors and regulating EGF signaling, and GM1 ganglioside is important for the formation of the GDNF-receptor complex in dopaminergic neurons. Results demonstrated that GM1 augments an epigenetic gene regulation mechanism for neuronal cell lineage differentiation.

The mitochondrial fission protein, dynamin-related protein-1 (Drp1), is GD3-binding protein, and GD3 regulates mitochondrial dynamics Furthermore, GM1 ganglioside promotes neuronal gene expression by an epigenetic regulatory mechanism. Thus, results indicated that multifunctional gangliosides modulate lipid microdomains to regulate functions of important molecules on plasma membrane, mitochondrial membrane, and nuclear membrane.

2. Pharmaceutical Compositions

Compositions, e.g., pharmaceutical compositions, including gangliosides are also provided.

The compositions, e.g., a GM1 containing composition, a GD3 containing composition, or a GM1 and GD3 containing composition, may be in the form of an injectable or infusible unit dose.

Examples of carriers or diluents usable for preparing compositions, including injectable and infusible doses, include diluents such as water, ethyl alcohol, macrogol, propylene glycol, ethoxylated isostearyl alcohol, polyoxyisostearyl alcohol and polyoxyethylene sorbitan fatty acid esters, pH adjusting agents or buffers such as sodium citrate, sodium acetate and sodium phosphate, stabilizers such as sodium pyrosultite, EDTA, thioglycolic acid and thiolactic acid, isotonic agents such as sodium chloride and glucose, local anesthetics such as procaine hydrochloride and lidocaine hydrochloride. Furthermore, usual solubilizing agents and analgesics may be added. Compositions can be prepared by adding such carriers to the active, following procedures well known to those of skill in the art. A thorough discussion of pharmaceutically acceptable excipients is available in REMINGTON'S PHARMACEUTICAL SCIENCES (Mack Pub. Co., N.J. 1991). The pharmaceutically acceptable formulations can easily be suspended in aqueous vehicles and introduced through conventional hypodermic needles or using infusion pumps. Prior to introduction, the formulations can be sterilized with, preferably, gamma radiation or electron beam sterilization.

Compositions described herein may be employed in combination with another medicament. The compositions can appear in conventional forms, for example, aerosols, solutions, suspensions, or topical applications, or in lyophilized form.

Typical compositions include GM1 gangliosides, GD3 gangliosides, or a combination thereof, and a pharmaceutically acceptable excipient which can be a carrier or a diluent. For example, the active agent(s) may be mixed with a carrier, or diluted by a carrier, or enclosed within a carrier. When the active agent is mixed with a carrier, or when the carrier serves as a diluent, it can be solid, semi-solid, or liquid material that acts as a vehicle, excipient, or medium for the active agent. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the art, such as glyceryl monostearate or glyceryl distearate, alone or mixed with a wax.

The formulations can be mixed with auxiliary agents which do not deleteriously react with the active agent(s). Such additives can include wetting agents, emulsifying and suspending agents, salt for influencing osmotic pressure, buffers and/or coloring substances preserving agents, sweetening agents or flavoring agents. The compositions can also be sterilized if desired.

If a liquid carrier is used, the preparation can be in the form of a liquid such as an aqueous liquid suspension or solution. Acceptable solvents or vehicles include sterilized water, Ringer's solution, or an isotonic aqueous saline solution.

The agent(s) may be prodded as a powder suitable for reconstitution with an appropriate solution as described above. Examples of these include, but are not limited to, freeze dried, rotary dried or spray dried powders, amorphous powders, granules, precipitates, or particulates. The composition can optionally contain stabilizers, pH modifiers, surfactants, bioavailability modifiers and combinations of these. A unit dosage form can be in individual containers or in multi-dose containers.

In one embodiment, the preparation can contain an agent, dissolved or suspended in a liquid carrier, such as an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens. For example, in addition to solubility, efficient delivery to the CNS following intranasal administration may be dependent on membrane permeability. For enzymes where paracellular transport is hindered due to size and polarity, improving membrane permeability may enhance extracellular mechanisms of transport to the CNS along olfactory and trigeminal nerves. One approach to modifying membrane permeability within the nasal epithelium is by using permeation enhancers, such as surfactants, e.g., lauroylcarnitine (LC), bile salts, lipids, cyclodextrins, polymers, or tight junction modifiers.

Generally, the active agents are dispensed in unit dosage form including the active ingredient together with a pharmaceutically acceptable carrier per unit dosage. Usually, dosage forms suitable for nasal administration include from about 125 μg to about 125 mg, e.g., from about 250 μg to about 50 mg, or from about 2.5 mg to about 25 mg, of the compounds admixed with a pharmaceutically acceptable carrier or diluent.

The gangliosides can be delivered in the intranasal methods of treatment in suitable dose ranges, generally about 0.01 to 100 mg/kg/day. In one embodiment, the gangliosides employed for intranasal delivery is at 5 mg/kg/day.

Dosage forms can be administered daily, or more than once a day, such as twice or thrice daily. Alternatively, dosage forms can be administered less frequently than daily, such as every other day, or weekly, if found to be advisable by a prescribing physician.

B. Methods of Treatment

Methods are provided for treating and/or preventing neurodegenerative disease in a subject. The methods can include administering the CNS of a mammal in need of treatment an effective amount of a pharmaceutical composition having a GM1 gangliosides. The methods can include administering to the CNS of a mammal in need of treatment an effective amount of a pharmaceutical composition having GD3 gangliosides. The method can include administering the CNS of a mammal in need of treatment an effective amount of a pharmaceutical composition having a combination of GM1 and GD3 gangliosides.

GD3 is typically used to increase stemness, while GM1 is typically used to sustain neuronal function. Thus, in some embodiments, such as in early to moderate stages of neurodegenerative diseases, GM1 can be administered alone, and is e.g., sufficient to maintain neuronal functions. In some embodiments, such as at more severe stages of diseases, GD3 can be first administered to amplify NSCs and then GM1 can optionally, but preferably be administered to support neuronal differentiation of NSCs. For example, in treatment for depression, GD3 may need first, then GM1 may or may not be needed. For schizophrenia patients, GM1 may be efficient.

1. Methods of Administration

Any route of ganglioside administration may be employed so long as that route and the amount administered are therapeutically useful.

a. Intranasal Administration

Subcutaneous or intramuscular injection of ganglioside of GM1 alone to treat central nervous system disorders has been tried with inconsistent outcomes. It is well known that gangliosides form micelles and are normally not permeable through the blood-brain barrier. So far, intracerebroventricular (icv) administration is the most reliable method to deliver gangliosides into the brain, however this method is invasive.

Thus, in preferred embodiments, particularly those in which brain delivery is important, the method of administration is intranasal. Despite the immense network of the cerebral vasculature, systemic delivery of therapeutics to the CNS is not effective for greater than 98% of small molecules and for nearly 100% of large molecules (Pardridge, *NeuroRx,* 2:3 (2005)). The lack of effectiveness is due to the presence of the blood-brain barrier (BBB), which prevents most foreign substances, even many beneficial therapeutics, from entering the brain from the circulating blood. While certain small molecule, peptide, and protein therapeutics given systemically reach the brain parenchyma by crossing the BBB (Banks, *Biopolymers,* 90:589 (2008)), generally high systemic doses are needed to achieve therapeutic levels, which can lead to adverse effects in the body. Therapeutics can be introduced directly into the CNS by intracerebroventricular or intraparenchymal injections; however, for multiple dosing regimens both delivery methods are invasive, risky, and expensive techniques requiring surgical expertise. Additional limitations to the utility of these methods are inadequate CNS exposure due to slow diffusion from the injection site and rapid turnover of the cerebrospinal fluid (CSF). Intranasal delivery has come to the forefront as an alternative to invasive delivery methods to bypass the BBB and rapidly target therapeutics directly to the CNS utilizing pathways along olfactory and trigeminal nerves innervating the nasal passages (Frey II, *Drug Del. Tech.,* 2:46 (2002); Thorne et al., *Neuroscience,* 127:481 (2004); Dhanda et al., *Drug Del. Tech.,* 5:64 (2005)). See also, Pardridge, *NeuroRx,* 2(1):3-14. doi: 10.1602/neurorx.2.1.3. PMID: 15717053; Pubmed PMCID: PMC539316 (2005), Banks, *Biopolymer,* 90:589-594 (2008)).

Stem cell therapy for patients with neurodegenerative disease and conditions has been proposed, however, the activation of endogenous neuronal stem cells (NSC) has been presented as a safer option. Activation of adult neurogenesis is known to be promoted by neurotrophic factors whose signaling is dependent on their lipid environment. For example, as discussed herein GD3 gangliosides modulate NSC self-renewal by interacting with EGF receptors and regulating EGF signaling, and GM1 ganglioside is necessary for the formation of the GDNF-receptor complex in dopaminergic neurons. Moreover, this demonstrates that GM1 augments an epigenetic gene regulation mechanism for neuronal cell lineage differentiation.

For this reason, a method is disclosed that involves intranasal infusion of gangliosides GM1 and GD3 into brain tissue to reduce concentrations of cytotoxic proteins and promote neurogenesis for the treatment of neurodegenerative diseases. This can involve administering an effective amount of a pharmaceutical composition having a combination of GM1 and GD3 gangliosides to the CNS of a mammal in need of. The method provides neuroprotective and neurorestorative effects of a glycolipid compositions for patients with neurodegenerative diseases, such as Alzheimer's disease (AD) and Parkinson's disease (PD). Specifically, the method provides a functional role of gangliosides (FIGS. 1A and 1B), a group of glycosphingolipids (GSLs) abundant in the nervous system, in modulating oligomerization and aggregation of cytotoxic proteins, including amyloid β-peptide (Aβ) and alpha-synuclein (aSyn), that are the major pathologic hallmarks of cell death in AD and PD. In addition, the method provides the promotion of neurogenesis in damaged brains by gangliosides.

In some embodiments, intranasal delivery may be accomplished as described in U.S. Pat. No. 8,609,088, the disclosure of which is specifically incorporated by reference herein.

Pathways for Delivery

An accumulating body of evidence demonstrates that pathways involving nerves connecting the nasal passages to the brain and spinal cord are important. In addition, pathways involving the vasculature, cerebrospinal fluid, and lymphatic system have been implicated in the transport of molecules from the nasal cavity to the CNS. It is likely that a combination of these pathways is responsible, although one pathway may predominate, depending on the properties of the therapeutic, the characteristics of the formulation, and the delivery device used.

Therapeutics may rapidly gain access to the CNS following intranasal administration along olfactory nerve pathways leading from the nasal cavity directly to the CNS. Olfactory nerve pathways are a component of intranasal delivery, evidenced by the fact that fluorescent tracers are associated with olfactory nerves as they traverse the cribriform plate (Jansson et al., *J. Drug Target,* 10:379 (2002)), drug concentrations in the olfactory bulbs are generally among the highest CNS concentrations observed (Thorne et al., *Neuroscience,* 127:481 (2004); Banks et al., *J. Pharmacol. Exp. Ther.,* 309:469 (2004); Graff et al., *Pharm. Res.,* 22:235 (2005a); Nonaka et al., *J. Pharmacol. Exp. Ther.,* 325:513 (2008); Ross et al., *J. Neuroimmunol.,* 151:66 (2004), Ross et al., *Neurosci. Lett.,* 439: 30 (2008); Thorne et al., *Neuroscience,* 152:785 (2008)), and a strong, positive correlation exists between concentrations in the olfactory epithelium and olfactory bulbs (Dhuria et al., *J. Pharmacol. Exp. Ther.,* 328:312 (2009a)).

Olfactory pathways arise in the upper portion of the nasal passages, in the olfactory region, where olfactory receptor neurons (ORNs) are interspersed among supporting cells (sustentacular cells), microvillar cells, and basal cells. ORNs mediate the sense of smell by conveying sensory information from the peripheral environment to the CNS (Clerico et al., In: Doty R L, editor. Handbook of olfaction and gustation. 2nd edition. New York: Marcel Dekker, Inc. pp. 1-16 (2003)). Beneath the epithelium, the lamina propria contains mucus secreting Bowman's glands, axons, blood vessels, lymphatic vessels, and connective tissue. The dendrites of ORNs extend into the mucous layer of the olfactory epithelium, while axons of these bipolar neurons extend centrally through the lamina propria and through perforations in the cribriform plate of the ethmoid bone, which separates the nasal and cranial cavities. The axons of ORNs pass through the subarachnoid space containing CSF and terminate on mitral cells in the olfactory bulbs. From there, neural projections extend to multiple brain regions including the olfactory tract, anterior olfactory nucleus, piriform cortex, amygdala, and hypothalamus (Buck, In: Kandel E R, Schwartz J H, Jessell T M, editors. Principles of neural science. 4th edition. New York: McGraw-Hill Companies. pp. 625-652 (2000)). In addition to ORNs, chemosensory neurons located at the anterior tip of the nasal cavity in the Grueneberg ganglion lead into the olfactory bulbs (Fuss et al., *Eur. J. Neurosci.,* 22:2649 (2005); Koos et al., *Neuroreport,* 16:1929 (2005)).

The unique characteristics of the ORNs contribute to a dynamic cellular environment important for intranasal delivery to the CNS. Due to the direct contact with toxins in the external environment, ORNs regenerate every 3-4 weeks from basal cells residing in the olfactory epithelium (Mackay-Sim, In: Doty R L, editor. Handbook of olfaction and gustation. 2nd edition. New York: Marcel Dekker, Inc. pp. 93-113 (2003)). Special Schwann cell-like cells called olfactory ensheathing cells (OECs) envelope the axons of ORNs and have an important role in axonal regeneration, regrowth, and remyelination (Field et al., *J. Neurocytol.,* 32:317 (2003), Li et al., *Glia,* 52:245 (2005a), Li et al., *J. Neurocytol.,* 34:343 (2005b)). The OECs create continuous, fluid-filled perineurial channels that, interestingly, remain open, despite the degeneration and regeneration of ORNs (Williams et al., *J. Comp. Neurol.,* 470:50 (2004)).

Given the unique environment of the olfactory epithelium, it is possible for intranasally administered therapeutics to reach the CNS via extracellular or intracellular mechanisms of transport along olfactory nerves. Extracellular transport mechanisms involve the rapid movement of molecules between cells in the nasal epithelium, requiring only several minutes to 30 minutes for a drug to reach the olfactory bulbs and other areas of the CNS after intranasal administration (Frey II, *Drug Del. Tech.,* 2:46 (2002); Balin et al., *J. Comp. Neurol.,* 251:260-280 (1986)). Transport likely involves bulk flow mechanisms (Thorne et al., *Clin. Pharmacokinet.,* 40:907 (2001), Thorne et al., *Neuroscience,* 127:481 (2004)) within the channels created by the OECs. Drugs may also be propelled within these channels by the structural changes that occur during depolarization and axonal propagation of the action potential in adjacent axons (Luzzati et al., J. Mol. Biol., 343:199 (2004)). Intracellular transport mechanisms involve the uptake of molecules into ORNs by passive diffusion, receptor-mediated endocytosis or adsorptive endocytosis, followed by slower axonal transport, taking several hours to days for a drug to appear in the olfactory bulbs and other brain areas (Baker et al., *Exp. Brain Res.,* 63:461 (1986); Broadwell et al., *J. Comp. Neurol.,* 242:632 (1985).; Kristensson et al., *Acta Neuropathol* (Berl), 19:145 (1971)). Intracellular transport in ORNs has been demonstrated for small, lipophilic molecules such as gold particles (de Lorenzo, In: Wolstenholme G E W, Knight J, editors. Taste and smell in vertebrates. London:

Churchill. pp. 151-175 (1970); Gopinath et al., *Current Ther. Res.,* 23:596 (1978)), aluminum salts (Perl et al., *Lancet,* 1:1028 (1987)), and for substances with receptors on ORNs such as WGA-HRP (Thorne et al., *Brain Res.,* 692:278 (1995); Baker et al., *Exp. Brain Res.,* 63:461 (1986); Itaya et al., *Brain Res.,* 398:397 (1986); Shipley, *Brain Res. Bull.,* 15:129 (1985)). Intracellular mechanisms, while important for certain therapeutics, are not likely to be the predominant mode of transport into the CNS. While some large molecules, such as galanin-like peptide (CALP), exhibit saturable transport pathways into the CNS (Nonaka et al., *J. Pharmacol. Exp. Ther.,* 325:513 (2008)), for other large molecules such as NGF and insulin-like growth factor-I (IGF-I), intranasal delivery into the brain is nonsaturable and not receptor mediated (Thorne et al., *Neuroscience,* 127:481 (2004); Chen et al., *J. Alzheimers Dis.,* 1:35 (1998); Zhao et al., *Chin. Med. Sci. J.,* 19:257 (2004)).

An often overlooked but important pathway connecting the nasal passages to the CNS involves the trigeminal nerve, which innervates the respiratory and olfactory epithelium of the nasal passages and enters the CNS in the pons (Clerico et al., In: Doty R L, editor. Handbook of olfaction and gustation. 2nd edition. New York: Marcel Dekker, Inc. pp. 1-16 (2003); Graff et al., *Pharm. Res.,* 22:86 (2005b)). Interestingly, a small portion of the trigeminal nerve also terminates in the olfactory bulbs (Schaefer et al., *J. Comp. Neurol.,* 444:221 (2002)). The cellular composition of the respiratory region of the nasal passages is different from that of the olfactory region, with ciliated epithelial cells distributed among mucus secreting goblet cell. These cells contribute to mucociliary clearance mechanisms that remove mucus along with foreign substances from the nasal cavity to the nasopharynx. The trigeminal nerve conveys sensory information from the nasal cavity, the oral cavity, the eyelids, and the cornea, to the CNS via the ophthalmic division (V1), the maxillary division (V2), or the mandibular division (V3) of the trigeminal nerve (Clerico et al., In: Doty R L, editor. Handbook of olfaction and gustation. 2nd edition. New York: Marcel Dekker, Inc. pp. 1-16 (2003); Gray, 15th revised edition (Classic Collectors edition). New York: Bounty Books (1978)). Branches from the ophthalmic division of the trigeminal nerve provide innervation to the dorsal nasal mucosa and the anterior portion of the nose, while branches of the maxillary division provide innervation to the lateral walls of the nasal mucosa. The mandibular division of the trigeminal nerve extends to the lower jaw and teeth, with no direct neural inputs to the nasal cavity. The three branches of the trigeminal nerve come together at the trigeminal ganglion and extend centrally to enter the brain at the level of the ports, terminating in the spinal trigeminal nuclei in the brain stem. A unique feature of the trigeminal nerve is that it enters the brain from the respiratory epithelium of the nasal passages at two sites: (1) through the anterior lacerated foramen near the pons and (2) through the cribriform: plate near the olfactory bulbs, creating entry points into both caudal and rostral brain areas following intranasal administration. It is also likely that other nerves that innervate the face and head, such as the facial nerve, or other sensory structures in the nasal cavity, such as the Grueneberg ganglion, may provide entry points for intranasally applied therapeutics into the CNS.

Traditionally, the intranasal route of administration has been utilized to deliver drugs to the systemic circulation via absorption into the capillary blood vessels underlying the nasal mucosa. The nasal mucosa is highly vascular, receiving its blood supply from branches of the maxillary, ophthalmic and facial arteries, which arise from the carotid artery (Clerico et al., In: Doty R L, editor. Handbook of olfaction and gustation. 2nd edition. New York: Marcel Dekker, Inc. pp. 1-16 (2003); Cauna, In: Proctor D F, Andersen I, editors. Amsterdam: Elsevier Biomedical Press. pp. 45-69 (1982)). The olfactory mucosa receives blood from small branches of the ophthalmic artery, whereas the respiratory mucosa receives blood from a large caliber arterial branch of the maxillary artery (DeSesso, *Qual. Assur.,* 2:213 (1993)). The relative density of blood vessels is greater in the respiratory mucosa compared to the olfactory mucosa, making the former region an ideal site for absorption into the blood (DeSesso, *Qual. Assur.,* 2:213 (1993)). The vasculature in the respiratory region contains a mix of continuous and fenestrated endothelia (Grevers et al., *Arch. Otorhinolaryngol.,* 244:55 (1987); Van Diest et al., *J. Anat.,* 128:293 (1979)), allowing both small and large molecules to enter the systemic circulation following nasal administration.

Delivery to the CNS following absorption into the systemic circulation and subsequent transport across the BBB is possible, especially for small, lipophilic drugs, which more easily enter the blood stream and cross the BBB compared to large, hydrophilic therapeutics such as peptides and proteins.

Increasing evidence is emerging that mechanisms involving channels associated with blood vessels, or perivascular channels, are involved in intranasal drug delivery to the CNS. Perivascular spaces are bound by the outermost layer of blood vessels and the basement membrane of the surrounding tissue (Pollock et al., *J. Anat.,* 191:337 (1997)). These perivascular spaces act as a lymphatic system for the brain, where neuron-derived substances are cleared from brain interstitial fluid by entering perivascular channels associated with cerebral blood vessels. Perivascular transport is due to bulk flow mechanisms, as opposed to diffusion alone (Cserr et al., *Am. J. Physiol.,* 240:F319 (1981); Groothuis et al., *J. Cereb. Blood Flow Metab.,* 27:43 (2007)), and arterial pulsations are also a driving force for perivascular transport (Rennels et al., *Brain Res.,* 326:47 (1985), Rennels et al., *Adv. Neurol.,* 52:431 (1990)). Intranasally applied drugs can move into perivascular spaces in the nasal passages or after reaching the brain and the widespread distribution observed within the CNS could be due to perivascular transport mechanisms (Thorne et al., *Neuroscience,* 127:481 (2004)).

Pathways connecting the subarachnoid space containing CSF, perineurial spaces encompassing olfactory nerves, and the nasal lymphatics are important for CSF drainage and these same pathways provide access for intranasally applied therapeutics to the CSF and other areas of the CNS. Several studies document that tracers injected into the CSF in the cerebral ventricles or subarachnoid space drain to the underside of the olfactory bulbs into channels associated with olfactory nerves traversing the cribriform plate and reach the nasal lymphatic system and cervical lymph nodes (Bradbury et al., *J. Physiol.,* 339:519 (1983); Hatterer et al., *Blood,* 107:806 (2006); Johnston et al., *Cerebrospinal Fluid Res.,* 1:2 (2004); Kida et al., *Neuropathol. Appl. Neurobiol.,* 19:480 (1993); Walter et al., *Arch. Histol. Cytol.,* 69:37 (2006a); Walter et al., *Neuropathol. Appl. Neurobiol.,* 32:388 (2006b)). Drugs can access the CNS via these same pathways after intranasal administration, moving from the nasal passages to the CSF to the brain interstitial spaces and perivascular spaces for distribution throughout the brain. These drainage pathways are significant in a number of animal species (sheep, rabbits, and rats) accounting for approximately 50% of CSF clearance (Bradbury et al., *Am.*

*J. Physiol.,* 240:F329 (1981); Boulton et al., *Am. J. Physiol.,* 276:R818 (1999); Boulton et al., *Neuropathol. Appl. Neurobiol.,* 22:325 (1996); Cserr et al., *Brain Pathol.,* 2:269 (1992)). Pathways between the nasal passages and the CSF are still important and functional in humans, evidenced by the fact that therapeutics are directly delivered to the CSF following intranasal delivery, without entering the blood to an appreciable extent (Born et al., *Nat. Neurosci.,* 5:514 (2002)). A number of intranasal studies demonstrate that drugs gain direct access to the CSF from the nasal cavity, followed by subsequent distribution to the brain and spinal cord. Many intranasally applied molecules rapidly enter the CSF, and this transport is dependent on the lipophilicity, molecular weight, and degree of ionization of the molecules (Dhanda et al., *Drug Del. Tech.,* 5:64 (2005); Born et al., *Nat. Neurosci.,* 5:514 (2002); Kumar et al., *Curr. Sci.,* 43:435 (1974); Sakane et al., *J. Pharm. Pharmacol.,* 47:379 (1995); Sakane et al., *J. Pharm. Pharmacol.,* 46:378 (1994); Wang et al., *Int. J. Pharm.,* 341:20 (2007)). Assessing distribution into the CSF can provide information on the mechanism of intranasal delivery.

Exemplary Intranasal Administration Methods

Optimal delivery to the CNS along neural pathways is associated with delivery of the agent to the upper third of the nasal cavity (Hanson et al., *BMC Neurosci.,* 9:S5 (2008)). Although a supine position may be employed another position for targeting the olfactory region is with the "praying to Mecca" position, with the head down-and-forward. A supine position with the head angle at 70° or 90° may be suitable for efficient delivery to the CSF using a tube inserted into the nostrils to deliver the drug via intranasal administration (van den Berg et al., *J. Neurosci. Methods,* 116:99 (2002)).

For intranasal drug administration nose drops may be administered over a period of 10-20 minutes to alternating nostrils every 1-2 minutes to allow the solution to be absorbed into the nasal epithelium (Thorne et al., *Neuroscience,* 127:481 (2004); Capsoni et al., *Proc. Natl. Acad. Sci.* USA, 99:12432 (2002); Ross et al., *J. Neuroimmunol.,* 151:66 (2004); Ross et al., *Neurosci. Lett.,* 439: 30 (2008); Dhuria et al., *J. Pharmacol. Exp. Ther.,* 328:312 (2009a); Dhuria et al., *J. Pharm. Sci.,* 98:2501 (2009b); Francis et al., *Brain,* 131:3311 (2008); Martinez et al., *Neuroscience,* 157:908 (2008)). This noninvasive method does not involve inserting the device into the nostril, instead, drops are placed at the opening of the nostril, allowing the individual to sniff the drop into the nasal cavity. Other administration methods in anesthetized individual involve sealing the esophagus and inserting a breathing tube into the trachea to prevent the nasal formulation from being swallowed and to eliminate issues related to respiratory distress (Chow et al., *J. Pharm. Sci.,* 88:754 (1999); Chow et al., *J. Pharm. Sci.,* 90:1729 (2001); Fliedner et al., *Endocrinology.,* 17:2088 (2006); Dahlin et al., *Eur. J. Pharm. Sci.,* 14:75 (2001)). Flexible tubing can be inserted into the nostrils for localized delivery of a small volume of the drug solution to the respiratory or olfactory epithelia, depending on the length of the tubing (Chow et al., *J. Pharm. Sci.,* 88:754 (1999); Van den Berg et al., *J. Drug Target,* 11:325 (2003); van den Berg et al., *Pharm. Res.,* 21:799 (2004a); Banks et al., *J. Pharmacol. Exp. Ther.,* 309:469 (2004); van den Berg et al., *J. Neurosci. Methods,* 116:99 (2002); Vyas et al., *J. Pharm. Sci.,* 95:570 (2006a); Charlton et al., *J. Drug Target,* 15:370 (2007a); Gao et al., *Int. J. Pharm.,* 340:207 (2007a)).

Nasal delivery devices, such as sprays, nose droppers or needle-less syringes, may be employed to target the agent to different regions of the nasal cavity. OptiMist™ is a breath actuated device that targets liquid or powder nasal formulations to the nasal cavity, including the olfactory region, without deposition in the lungs or esophagus (Djupesland et al., *Laryngoscope,* 116:466 (2006)). The ViaNase™ device can also be used to target a nasal spray to the olfactory and respiratory epithelia of the nasal cavity. Nasal drops tend to deposit on the nasal floor and are subjected to rapid mucociliary clearance, while nasal sprays are distributed to the middle meatus of the nasal mucosa (Scheibe et al., *Arch. Otolaryngol. Head Neck Surg.,* 134:643 (2008)).

b. Other Routes of Administration

Other routes of administration to the CNS include intrathecal and intracranial. Intracranial administration may be to the cisterna magna or ventricle. The term "cisterna magna" is intended to include access to the space around and below the cerebellum via the opening between the skull and the top of the spine. The term "cerebral ventricle" is intended to include the cavities in the brain that are continuous with the central canal of the spinal cord. The gangliosides delivered in the intrathecal methods of treatment can be administered through any convenient route commonly used for intrathecal administration. For example, the intrathecal administration may be via a slow infusion of the formulation for about an hour.

The intrathecal administration can include introducing the composition into the lumbar area. Any such administration may be via a bolus injection. Depending on the severity of the symptoms and the responsiveness of the subject to the therapy, the bolus injection may be administered once per week, once per month, once every 6 months or annually. In other embodiments, the intrathecal administration is achieved by use of an infusion pump. Those of skill in the art are aware of devices that may be used to effect intrathecal administration of a composition. The composition may be intrathecally given, for example, by a single injection, or continuous infusion. It should be understood that the dosage treatment may be in the form of a single dose administration or multiple doses.

As used herein, the term "intrathecal administration" is intended to include delivering a pharmaceutical composition directly into the cerebrospinal fluid of a subject, by techniques including lateral cerebroventricular injection through a burrhole or cisternal or lumbar puncture or the like. The term "lumbar region" is intended to include the area between the third and fourth lumbar (lower back) vertebrae and, more inclusively, the 2-S1 region of the spine.

Administration to any of the above-mentioned sites can be achieved by direct injection of the composition or by the use of infusion pumps. For injection, the composition can be formulated in liquid solutions, e.g., in physiologically compatible buffers such as Hank's solution, Ringer's solution or phosphate buffer. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

In some embodiments, the gangliosides are administered by intracerebroventricular (icv) injection into the brain of a subject. The injection can be made, for example, through a burr hole made in the subject's skull. In another embodiment, the composition is administered through a surgically inserted shunt into the cerebral ventricle of a subject. For example, the injection can be made into the lateral ventricles, which are larger, even though injection into the third and fourth smaller ventricles can also be made. In yet another embodiment, the composition is administered by injection into the cisterna magna or lumbar area of a subject.

In some embodiments, the compounds(s) is in an optical or ophthalmic formulation, preferably which is administered directly to the eye. For example, the compounds may be effectively used, as needed, by methods which include administering an effective amount of the composition to an eye, e.g., in need of neural regeneration in the retina. The administering step may be repeated as needed to provide treatment to such eye. The mode of administration of the present composition depends on the form of the composition. Forms of topical administration to the eye include, but are not limited to, in the form of solutions, suspensions, ointments, creams, or solid inserts. For example, if the composition is a solution, drops of the composition may be applied to the eye, e.g., from a conventional eye dropper. Local ocular administration includes subconjunctival, retrobulbar, intracameral, intravitreal methods of administration. In general, the compositions may be applied to the surface of the eye in substantially the same way as conventional ophthalmic compositions are applied.

2. Exemplary Diseases for Treatment

Neurodegenerative diseases to be treated can include any disease or disorder or symptoms or causes or effects thereof involving the damage or deterioration of neurons. Neurodegenerative diseases can include, but are not limited to, Alexander Disease, Alper's Disease, Alzheimer's Disease, Amyotrophic Lateral Sclerosis, Ataxia Telangiectasia, Canavan Disease, Cockayne Syndrome, Corticobasal Degeneration, Creutzfeldt-Jakob Disease, Huntington's Disease, Kennedy's Disease, Krabbe Disease, Lewy Body Dementia, Machado-Joseph Disease, Multiple Sclerosis, Parkinson's Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, Tabes Dorsalis or any other condition associated with damaged neurons. Other neurodegenerative conditions can include or be caused by traumatic spinal cord injury, ischemic spinal cord injury, stroke, traumatic brain injury, and hereditary conditions. Other diseases to be treated include, but are not limited to, mental disorders such as depression and schizophrenia. Other diseases and injuries in the head which may be treated according to the disclosed compositions and methods include nose, eye and ear dysfunctions and degeneration, including by injury or disease.

a. Parkinson's Disease

In a particular embodiment, the disclosed compositions and methods are used to treat a subject with Parkinson's disease or suffering from parkinsonism or parkinson's syndrome. PD is a degenerative disorder of the central nervous system. In some embodiments, the subject exhibits one or more of the PD clinical symptoms, one or more PD molecular symptoms, or a combination thereof, such as those discussed herein and elsewhere. Symptoms of PD are well known in the art and reviewed in Jankovic, et al., J. Neurol. *Neurosurg. Psychiatr.,* 79(4): 368-76 (2007). The motor symptoms of Parkinson's disease result from the death of dopamine-generating cells in the substantia nigra, a region of the midbrain. The cause of the cell death remains unknown. Early in the course of the disease, the most obvious symptoms are movement-related and include, but are not limited to, shaking, rigidity, slowness of movement and difficulty with walking and gait. In particular, four motor symptoms considered hallmarks of PD are tremor, rigidity, slowness of movement, and postural instability. The main motor symptoms are collectively called parkinsonism, or a "parkinsonian syndrome".

Later, thinking and behavioral problems may arise and can range from mild to severe, with dementia commonly occurring in the advanced stages of the disease, whereas depression is the most common psychiatric symptom. Other common neuropsychiatric disturbances include disorders of speech, cognition, mood, behavior, and thought. Cognitive disturbances, which can occur in the initial stages of the disease and sometimes prior to diagnosis, include executive dysfunction, which can include problems with planning, cognitive flexibility, abstract thinking, rule acquisition, initiating appropriate actions and inhibiting inappropriate actions, and selecting relevant sensory information; fluctuations in attention and slowed cognitive speed; and memory loss.

Other symptoms include sensory, sleep and emotional problems. In fact, disturbances of sleep and wake are among the most common and disabling non-motor manifestations of PD, affecting as many as 90% of patients (Videnovic, et al., *JAMA Neurol.* doi:10.1001/jamaneurol. 2013.6239, published online Feb. 24, (2014)).

A physician's diagnosis of PD typically comes from a combination of medical history and neurological examination. Brain scans of people with PD typically look normal, but can be used to rule out disorders that could give rise to similar symptoms. Although no lab test exists for PD, medical organizations have created diagnostic criteria to facilitate and standardize the diagnostic process. See, for example, the UK Parkinson's Disease Society Brain Bank, the U.S. National Institute of Neurological Disorders and Stroke, and the PD Society Brain Bank which all provide criteria for diagnosing PD.

Parkinson's disease is more common in older people, with most cases occurring after the age of 50. There is no cure for PD, and the disease is most typically managed using one or a combination of levodopa (usually combined with a dopa decarboxylase inhibitor or COMT inhibitor), dopamine agonists and MAO-B inhibitors. Other common agents include amantadine and anticholinergics for treating motor symptoms, clozapine for treating psychosis, cholinesterase inhibitors for treating dementia, and modafinil for treating daytime sleepiness. Surgery and deep brain stimulation can be used, most typically when drugs are no longer effective. Gene therapies, stem cell transplants, neuroprotective agents, are also being developed as treatment options for PD.

In some embodiments, the subject exhibits one or more of the PD clinical symptoms such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having PD by exhibiting clinical (e.g., physical) symptoms of the disease. In some patients the appearance of a sleep-related disorder precedes a clinical diagnosis of PD. Therefore, in some embodiments, the compounds or compositions disclosed herein are administered prior to a clinical diagnosis of PD.

b. Alzheimer's Disease

The methods disclosed herein can be used to treat a subject with Alzheimer's disease Alzheimer's disease (AD) is the most common form of dementia. Although the cause and progression of AD are not entirely understood, research indicates plaques and tangles in the brain play a pathophysiological role. Current treatments only help with the symptoms of the disease and there are no available treatments that stop or reverse the progression of the disease.

In some embodiments, the subject exhibits one or more of the AD clinical symptoms, one or more AD molecular symptoms, or a combination thereof, such as those discussed herein and elsewhere. Clinical symptoms of AD are known in the art. Although Alzheimer's disease develops differently for every individual, there are many common symptoms. Early symptoms are often mistakenly thought to be "age-related" concerns, or manifestations of stress. One of the most common early symptoms is short term memory loss. Moderate stage symptoms can include, for example, increased memory loss and confusion, problems recognizing family and friends, continuously repeating stories, favorite wants, or motions, difficulty doing things that have multiple steps, like getting dressed, and/or lack of concern for hygiene and appearance. Severe stage symptoms can include, for example, inability to recognize oneself or family, inability to communicate, lack of control over bowel and bladder, groaning, moaning, or grunting, and/or needing help with all activities of daily living. Other common symptoms can include confusion, irritability, aggression, mood swings, trouble with language, and long-term memory loss. Gradually, bodily functions are lost, ultimately leading to death.

When AD is suspected, the diagnosis is usually confirmed with tests that evaluate behavior and thinking abilities (e.g., cognitive testing), often followed by a brain scan if available. Assessment of intellectual functioning including memory testing and neuropsychological tests such as the mini-mental state examination (MMSE) are widely used to evaluate the cognitive impairments needed for diagnosis (Waldemar, et al., *Eur J Neurol.* 14(1):e1-26 (2007)). Neurological examination in early AD will usually provide normal results, except for obvious cognitive impairment, which may not differ from that resulting from other diseases processes, including other causes of dementia.

Examination of brain tissue can lead to a definitive diagnosis. AD develops for an unknown and variable amount of time before becoming fully apparent, and it can progress undiagnosed for years.

In some embodiments, the subject exhibits one or more of the AD clinical symptoms, one or more ALS molecular symptoms, or a combination thereof, such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having AD by exhibiting clinical (e.g., physical) symptoms of the disease. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having AD by exhibiting clinical (e.g., physical) symptoms of the disease. In some patients the appearance of sleep-related disorder precede a clinical diagnosis of AD. Therefore, in some embodiments, the compounds or compositions disclosed herein are administered prior to a clinical diagnosis of AD.

c. Amyotrophic Lateral Sclerosis

The methods disclosed herein can be used to treat a subject with amyotrophic lateral sclerosis. Amyotrophic lateral sclerosis (ALS) is a fatal motor neuron disease, affecting both the first and second order motor neurons. The progression of ALS is characterized by a degeneration of motor neurons associated with a demyelination in the anterior horn of the spinal cord. The etiology is only partially understood. Of the 5-10% familial cases, 20% carry a mutation of the superoxide dismutase 1 (SOD1) gene. Such a mutation is also present in 5% of the sporadic cases (Rowland, et al., *New Engl J Med,* 44:1688-1700 (2001)). Three to four percent 3%-4% of familial cases are due to pathogenic variants in either the TDP-43 or FUS gene (Mackenzie, et al., *Lancet Neurol.,* 9:995-1007 (2010)).

In some embodiments, the subject exhibits one or more of the ALS clinical symptoms, one or more ALS molecular symptoms, or a combination thereof, such as those discussed herein and elsewhere. Clinical symptoms of ALS are known in the art. For example, the earliest symptoms of ALS are typically weakness and/or muscle atrophy. Other early symptoms include trouble swallowing, cramping, or stiffness of affected muscles; muscle weakness affecting an arm or a leg; and/or slurred and nasal speech, and in some cases dementia.

To be diagnosed with ALS, a patient must have signs and symptoms of both upper and lower motor neuron damage that cannot be attributed to other causes. The diagnosis depends on progressive degeneration of upper (UMN) and lower (LMN) motor neurons findings by history and examination and is accurate 95% of the time when made by an experienced clinician (Gordon, *Aging and Disease,* 4(5): 295-310 (2013)). Electromyography can be used to confirm widespread lower motor neuron disease and exclude other diseases such as multifocal motor neuropathy with conduction block. Brain and spinal MRI rule out conditions that affect the UMN, including cervical spondylosis. Occasionally the brain MRI shows bilateral signal changes within the corticospinal tracts, a finding that is pathognomonic of ALS. The E1 Escorial criteria help standardize diagnosis for clinical research studies (Brooks, et al., *Amyotroph Lateral Scler Other Motor Neuron Disord,* 1:293-299 (2000)).

Over time, patients experience increasing difficulty moving, swallowing (dysphagia), and speaking or forming words (dysarthria). Symptoms of upper motor neuron involvement include tight and stiff muscles (spasticity) and exaggerated reflexes (hyperreflexia) including an overactive gag reflex. An abnormal reflex commonly called Babinski's sign also indicates upper motor neuron damage. Symptoms of lower motor neuron degeneration include muscle weakness and atrophy, muscle cramps, and fleeting twitches of muscles that can be seen under the skin (fasciculations). Degeneration of bulbar upper motor neurons can cause exaggeration of motor expressions of emotion.

Progression is subject-specific, however, eventually most patients are not able to walk or use their hands and arms. They also lose the ability to speak and swallow their food, and most end on a portable ventilator. The rate of progression can be measured using an outcome measure called the "ALS Functional Rating Scale Revised (ALSFRS-R)", a 12-item instrument administered as a clinical interview or patient-reported questionnaire that produces a score between 48 (normal function) and 0 (severe disability).

A survey-based study amongst clinicians showed that they rated a 20% change in the slope of the ALSFRS-R would be clinically meaningful (Castrillo-Viguera, et al., *Amyotroph Lateral Scler,* 11(1-2):178-80 (2010)). Therefore, in some embodiments, the composition is administered to a subject an amount effective to change in the slope of the ALSFRS-R of a subject 1%, 5%, 10%, 15%, 20%, or more. In some embodiments, the ALSFRS-R score of the subject is taken prior to, and one or more after initiation of treatment. In some embodiments, the ALSFRS-R score takes day, weeks, months, or more to improve.

In some embodiments, the subject exhibits one or more of the ALS clinical symptoms, one or more ALS molecular symptoms, or a combination thereof, such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having ALS by exhibiting clinical (e.g., physical) symptoms of the disease. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having ALS by exhibiting clinical (e.g., physical) symptoms of the disease. In some patients the appearance of sleep-related disorder precedes a clinical diagnosis of ALS. Therefore, in some embodiments, the compounds or compositions disclosed herein are administered prior to a clinical diagnosis of ALS. In some embodiments, a genetic test indicates that the subject has one or more genetic mutations associated with ALS.

d. Huntington's Disease

The methods disclosed herein can be used to treat subjects with Huntington's disease. Huntington's disease (HD) is a neurodegenerative genetic disorder that affects muscle coordination and leads to cognitive decline and psychiatric problems. The chronic pathology in HD leads to numerous associated troubles including cognitive dysfunctions, more specifically dysfunction in thought and mental representations, changes in reasoning, in judgment. HD is caused by an autosomal dominant mutation in either of an individual's two copies of the Huntingtin (H11) gene. Part of this gene is a repeated section called a trinucleotide repeat, which varies in length between individuals and may change length between generations. If the repeat is present in a healthy gene, a dynamic mutation may increase the repeat count and result in a defective gene. When the length of this repeated section reaches a certain threshold, it produces an altered form of the protein, called mutant Huntingtin protein (mHtt). The differing functions of these proteins are the cause of pathological changes which in turn cause the disease symptoms. The Huntington's disease mutation is genetically dominant and almost fully penetrant. Mutation of either of a person's HTT genes can cause the disease. Physical symptoms of Huntington's disease can begin at any age from infancy to old age, but usually begin between 35 and 44 years of age (Walker, et al., *Lancet,* 369 (9557):218-28 (2007)).

In some embodiments, the subject exhibits one or more of the HD clinical symptoms, one or more HD molecular symptoms, or a combination thereof, such as those discussed herein and elsewhere. Clinical symptoms of HD are known in the art and include behavioral disturbances including, but not limited to, hallucinations, irritability, moodiness, restlessness, fidgeting, paranoia, psychosis, suicidal thoughts, and suicide attempts; abnormal and/or unusual movements including, but not limited to, chorea, facial movements such as grimaces, head turning to shift eye position, quick, sudden, sometimes wild jerking movements of the arms, legs, face, and other body parts, slow, uncontrolled movements, unsteady gait, small unintentionally initiated or uncompleted motions, and lack of coordination; cognitive impairment and/or dementia-related symptoms including, but not limited to, disorientation and/or confusion, loss of judgment, loss of memory, personality changes, and speech changes; and other symptoms including anxiety, stress, tension, difficulty swallowing, speech impairment, rigidity, slow movements, tremor, malnutrition, and weight loss. Neuropsychiatric features are a core component of the disease.

Mutant Huntingtin is expressed throughout the body and associated with abnormalities in peripheral tissues that are directly caused by such expression outside the brain. These abnormalities include muscle atrophy, cardiac failure, impaired glucose tolerance, weight loss, osteoporosis and testicular atrophy.

A number of studies have examined the prevalence of the myriad of symptoms in subjects with Huntington's disease. Shiwach, *Acta Psychiatr Scand,* 90(4):241-6 (1994) reports the results of a retrospective study of 110 patients with Huntington disease in 30 families. The study found the minimal lifetime prevalence of depression to be 39%. The frequency of symptomatic schizophrenia was 9%, and significant personality change was found in 72% of the sample. The age at onset was highly variable. Some showed signs in the first decade and some not until over 60 years of age.

Rosenberg, et al., *J Med Genet.,* 32(8):600-4 (1995) describes a double-blind study on 33 persons at risk for HD who had applied for genetic testing. Significantly inferior cognitive functioning was disclosed in gene carriers by a battery of neuropsychologic tests covering attentional, visuospatial, learning, memory, and planning functions. Primarily, attentional, learning, and planning functions were affected.

Bamford, et al., *Neurology,* 45(10):1867-73 (1995) reports a prospective analysis of neuropsychologic performance and CT scans of 60 individuals with Huntington's disease. The study found that psychomotor skills showed the most significant consistent decline among cognitive functions assessed.

Marshall, et al., *Arch Neurol.,* 64(1):116-21 (2007) reports a study comparing psychiatric manifestations among 29 HD mutation carriers with no clinical symptoms, 20 HD mutation carriers with mild motor symptoms, 34 manifesting HD patients, and 171 nonmutation controls. The mild motor symptoms group and the manifesting HD group showed significantly higher scores for obsessive-compulsive behavior, interpersonal sensitivity, anxiety, paranoia, and psychoticism compared to the nonmutation control group. The mutation carriers without symptoms had higher scores for anxiety, paranoid ideation, and psychoticism compared to the nonmutation control group. The results indicated that individuals in the preclinical stage of HD exhibit specific psychiatric symptoms, and that additional symptoms may manifest later in the disease course. Suicidal ideation is a frequent finding in Huntington disease and physicians should be aware of increased suicide risk both in asymptomatic at-risk patients and symptomatic patients (Walker, et al., *Lancet,* 369 (9557):218-28 (2007)).

The mechanisms underlying HD are explored in Wang, et al., *Journal of Neuroscience,* 31 (41):14496-14507 (2011), which is discussed in more detail below. The study shows that mutant huntingtin (htt)-mediated toxicity in cells, mice, and humansis associated with loss of the type 1 melatonin receptor (MT1). High levels of MT1 receptor were found in mitochondria from the brains of wild-type mice but much less in brains from HD mice, melatonin inhibited mutant htt-induced caspase activation and preserved MT1 receptor expression. Therefore, in some embodiments, the compounds and compositions disclosed herein are administered to a subject with HD in an effective amount to treat one or more molecular symptoms of HD, for example, to reduce, delay or inhibit mutant htt-induced caspase activation; to reduce or prevent loss of MT1 receptor expression, particularly in the mitochondria of cell of the subject; or a combination thereof.

In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having HD by exhibiting clinical (e.g., physical) symptoms of the disease. Excessive unintentional movements of any part of the body are often the first clinical symptoms. If these are abrupt and have random timing and distribution, they suggest a diagnosis of HD. Cognitive or psychiatric symptoms are rarely the first diagnosed and are most typically only recognized in hindsight or when they develop further. Disease progression can be measured using the unified Huntington's disease rating scale which provides an overall rating system based on motor, behavioral, cognitive, and functional assessments (Huntington Study Group, *Movement Disorders,* 11(2):136-142 (1996)).

Medical imaging, such as computerized tomography (CT) and magnetic resonance imaging (MRI), and functional neuroimaging techniques, such as fMRI and PET, can supplement analysis of physical symptoms but are typically not diagnostic alone.

Genetic testing can be used to confirm a physical diagnosis if there is no family history of HD. Even before the onset of symptoms, genetic testing can confirm if an individual or embryo carries an expanded copy of the trinucleotide repeat in the HTT gene that causes the disease. The U.S. government sponsored genetic disease compendium, the Online Mendelian Inheritance in Man (OMIM) database, gives HD a phenotype number #143100. The gene/locus is huntingtin (HTT), and is located on Chromosome 4p16.3 with the Gene/Locus MIM number of 613004. Assignment of the 143100 number to the OMIM entry is because Huntington disease (HD) is a monogenetic disorder caused by an expanded trinucleotide repeat (CAG)n, encoding glutamine, in the gene encoding huntingtin (HTT; 613004) on chromosome 4p16.3. The genetic test for HD consists of a blood test which counts the numbers of CAG repeats in each of the HTT alleles.

Cutoffs for genetic testing are given as follows according to De Die-Smulders, et al., *Human Reproduction Update,* 19(3):304-315 (2013).

40 or more CAG repeats: full penetrance allele (FPA). A "positive test" or "positive result" generally refers to this case. A person who tests positive for the disease will develop HD sometime within their lifetime, provided he or she lives long enough for the disease to appear.

36 to 39 repeats: incomplete or reduced penetrance allele (RPA). It may cause symptoms, usually later in the adult life. There is a maximum risk of 60% that a person with an RPA will be symptomatic at the age of 65 years, and a 70% risk of being symptomatic at the age of 75 years.

27 to 35 repeats: intermediate allele (IA), or large normal allele. It is not associated with symptomatic disease in the tested individual, but may expand upon further inheritance to give symptoms in offspring. 26 or less repeats: Not associated with HD.

A positive result is considered different than a clinical diagnosis, since it may be obtained decades before the symptoms begin. The test can tell a person who originally had a 50 percent chance of inheriting the disease if their risk goes up to 100 percent or is eliminated.

Elsewhere, the range of repeat numbers for normal individual is 9 to 36, and 37 or greater in HD individuals (Duyao et al., *Nat Genet.,* 4(4):387-92 (1993)).

Therefore, in some embodiments, the subject has a "positive result", or is determined to have incomplete or reduced penetrance allele (RPA), or is determined to have intermediate allele (IA), or large normal allele by genetic testing, but does not exhibit any of the clinical symptoms, or the clinical symptoms are too mild for an affirmative medical diagnosis. In a particular embodiment, the subject has a "positive result" but does not exhibit any of the clinical symptoms, or the clinical symptoms are too mild for an affirmative medical diagnosis. Accordingly, in some embodiments, the compounds or compositions disclosed herein are administered prior to a clinical diagnosis of HD.

e. Multiple Sclerosis (MS)

In some embodiments, the subject has multiple sclerosis (MS). MS, also known as encephalomyelitis disseminata, is the most common demyelinating disease, in which the insulating covers of nerve cells in the brain and spinal cord are damaged. This damage disrupts the ability of parts of the nervous system to transmit signals, resulting in a range of signs and symptoms, including physical, mental, and sometimes psychiatric problems. Specific symptoms can include double vision, blindness in one eye, muscle weakness, and trouble with sensation or coordination. MS takes several forms, with new symptoms either occurring in isolated attacks (relapsing forms) or building up over time (progressive forms). Between attacks, symptoms may disappear completely, although permanent neurological problems often remain, especially as the disease advances.

While the cause is unclear, the underlying mechanism is thought to be either destruction by the immune system or failure of the myelin-producing cells. Proposed causes for this include genetics and environmental factors, such as viral infections. MS is usually diagnosed based on the presenting signs and symptoms and the results of supporting medical tests. In some embodiments, the subject has been diagnosed as having MS.

There is no known cure for multiple sclerosis. Treatments attempt to improve function after an attack and prevent new attacks. Medications used to treat MS, while modestly effective, can have side effects and be poorly tolerated. Physical therapy and occupational therapy can help with people's ability to function.

f. Traumatic Brain Injury

In another particular embodiment, the disclosed compositions are used to treat a subject suffering from traumatic brain injury (TBI). Traumatic brain injury occurs when an external mechanical force, typically head trauma, causes brain dysfunction.

Traumatic brain injury can have wide-ranging physical and psychological effects. Some signs or symptoms may appear immediately after the traumatic event, while others may not appear until days or weeks later. Symptoms of TBI include, but are not limited to, loss of consciousness; a state of being dazed, confused or disoriented; memory or concentration problems; headache, dizziness or loss of balance; nausea or vomiting; sensory problems such as blurred vision, ringing in the ears or a bad taste in the mouth;

sensitivity to light or sound; mood changes or mood swings; feeling depressed or anxious; fatigue or drowsiness; difficulty sleeping; sleeping more than usual, agitation, combativeness or other unusual behavior; slurred speech; inability to awaken from sleep; weakness or numbness in fingers and toes; loss of coordination; convulsions or seizures, dilation of one or both pupils of the eyes; and/or clear fluids draining from the nose or ears. In children, additional symptoms include change in eating or nursing habits; persistent crying and inability to be consoled; unusual or easy irritability; change in ability to pay attention; change in sleep habits; sad or depressed mood; and/or loss of interest in favorite toys or activities.

TBI can be diagnosed using the Glasgow Coma Scale, a 15-point test that helps a doctor or other emergency medical personnel assess the initial severity of a brain injury by checking a person's ability to follow directions and move their eyes and limbs. The coherence of speech also provides important clues. Abilities are scored numerically with higher scores indicating more mild injury Imaging such as computerized tomography (CT) and magnetic resonance imaging (MRI), as well as intracranial pressure monitoring can also be used to assist in the diagnoses by helping to identify the local(s) and extent of the trauma.

Conventional treatments for TBI include administration of agents such as diuretics, anti-seizer drugs, and coma-inducing drugs; surgery to remove clotted blood, repair skull fractures, and/or relieve pressure inside the skull.

g. Dementia With Lewy Bodies

In another particular embodiment, the disclosed compositions are used to treat a subject suffering from dementia with Lewy bodies (DLB) (also referred to as Lewy body dementia (LBD), diffuse Lewy body disease, cortical Lewy body disease, and senile dementia of Lewy type). Despite a name that suggests a histological diagnosis, DLB is now routinely defined by clinical symptoms, and can be clearly diagnosed as probable DLB in the absence of a histological diagnosis. The central, core, and suggestive features of DLB are known and described in, for example, (Bear, et al., *Neuroscience: exploring the brain,* 3rd ed. Philadelphia, PA: Lippincott Williams and Wilkins Publishers; (2007), Macijauskiene, et al., *Medicina* (Kaunas), 48(1):1-8 (2012)). Generally, the diagnostic criteria include a Parkinsonian movement disorder that either follows dementia (or does not precede it by more than one year), plus dementia, plus psychosis.

3. Combination Therapies

In some embodiments, a ganglioside composition is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of a ganglioside composition. The different active agents can have the same, or different mechanisms of action. In some embodiments, the combination results in an additive effect on the treatment of the disease or disorder. In some embodiments, the combinations result in a more than additive effect on the treatment of the disease or disorder. In some embodiments, the combination is two or more gangliosides (e.g., GD3 and GM1), alone or in further combination with one or more additional active agents.

In particular embodiments, a combination therapy includes a ganglioside composition and one or more conventional treatments for neurodegeneration, or for increasing or enhancing neuroprotection, such as those discussed herein. Exemplary neuroprotective agents are known in the art and include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin. In some embodiments, a ganglioside composition is administered to a subject in combination with a treatment that increase nerve regeneration.

In a particular embodiment, a ganglioside composition is administered to a subject in combination with a conventional treatment for Parkinson's disease, such as levodopa (usually combined with a dopa decarboxylase inhibitor or COMT inhibitor), a dopamine agonist, or an MAO-B inhibitor. Other common agents that can be used in combination the disclosed combinations include amantadine and anticholinergics for treating motor symptoms, clozapine for treating psychosis, cholinesterase inhibitors for treating dementia, and modafinil for treating daytime sleepiness.

In another particular embodiment, a ganglioside composition is administered to a subject in combination with a conventional treatment for AD, for example, acetylcholinesterase inhibitor such as tacrine, rivastigmine, galantamine or donepezil; or an NMDA receptor antagonist such as memantine, or an antipsychotic drug.

In another particular embodiment, a ganglioside composition is administered to a subject in combination with a conventional treatment for Huntington's disease, such as a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

In another particular embodiment, a ganglioside composition is administered to a subject in combination with a conventional treatment for ALS such as the antiexcitotoxin riluzole (RILUTEK®) (2-amino-6-(trifluoromethoxy) benzothiazole). Other medications, most used off-label, and interventions can reduce symptoms due to ALS. Some treatments improve quality of life and a few appear to extend life. Common ALS-related therapies are reviewed in Gordon, *Aging and Disease,* 4(5):295-310 (2013), which is specifically incorporated by reference herein in its entirety. Exemplary ALS treatments and interventions are provided Gordon, *Aging and Disease,* 4(5):295-310 (2013), which is specifically incorporated by reference herein in its entirety.

A number of other agents have been tested in one or more clinical trials with efficacies ranging from non-efficacious to promising. Exemplary agents are reviewed in Carlesi, et al., *Archives Italiennes de Biologie,* 149:151-167 (2011). For example, in some embodiments, a ganglioside composition, is administered to a subject in combination with an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f) oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

In another particular embodiment, a ganglioside composition is administered to a subject in combination with a conventional treatment for MS, for example, interferon beta-1a, interferon beta-1b, glatiramer acetate, mitoxantrone, natalizumab, fingolimod, teriflunomide, dimethyl fumarate, alemtuzumab, ocrelizumab, siponimod, cladribine, ozanimod, and ponesimod.

In another particular embodiment, a ganglioside composition is administered to a subject in combination with a conventional treatment for DLB, for example, an acetylcholinesterase inhibitor such as tacrine, rivastigmine, galantamine or donepezil; the N-methyl d-aspartate receptor antagonist memantine; dopaminergic therapy, for example, levodopa or selegiline; antipsychotics such as olanzapine or clozapine; REM disorder therapies such as clonazepam, melatonin, or quetiapine; anti-depression and antianxiety therapies such as selective serotonin reuptake inhibitors (citalopram, escitalopram, sertraline, paroxetine, etc.) or serotonin and noradrenaline reuptake inhibitors (venlafaxine, mirtazapine, and bupropion) Macijauskiene, et al., *Medicina* (Kaunas), 48(1):1-8 (2012).

In some embodiments, the active agent(s) is administered in combination with a co-therapy such as dietary changes with or without dietary supplements, exercise, psychological and/or psychosocial counseling, physical therapy, occupational therapy, and speech therapy.

The disclosure compositions and methods can be further understood by the following numbered paragraphs.

1. A method for treating or protecting a subject in need thereof from neurodegeneration comprising intranasally administering an effective amount of ganglioside GD3 and/or ganglioside GM1 into a brain of the subject.
2. The method of paragraph 1, wherein GD3 as administered in an effective amount to increase the number of neural stem cells (NSCs).
3. The method of paragraph 1, wherein GM1 is administered in an effective amount to increase neuronal differentiation.
4. The method of paragraphs 2 or 3, wherein GD3 is administered prior to GM1.
5. The method of paragraph 4, wherein administration of the GM1 is after GD3 has begun increasing the number of NSCs, and wherein GM1 increases differentiation of the NSCs.
6. The method of any one of paragraphs 1-5, comprising two or more administrations for GD3 and/or GM1.
7. The method of any one of paragraphs 2-6 comprising concurrent, sequential and overlapping, and/or sequential and non-overlapping administration of GM1 and GD3.
8. The method of any one of paragraphs 1, 3 or 6, wherein GM1 is administered alone and in the absence of GD3.
9. The method of any one of paragraphs 1, 2, or 6, wherein the GD3 is administered alone or in the absence of GM1.
10. The method of any one of paragraphs 1-9, wherein the neurodegeneration comprises damage or deterioration of neurons.
11. The method of any one of paragraphs 1-10, wherein the subject suffers from neurodegenerative disease or disorder, a mental disorder, or a neuronal disease or injury to the head or neck optionally to the eyes, nose, spine, or brain.
12. The method of paragraph 11, wherein the subject suffers from a neurodegenerative disease or disorder, wherein the neurodegenerative disease or disorder is selected from Alexander Disease, Alper's Disease, Alzheimer's Disease, Amyotrophic Lateral Sclerosis, Ataxia Telangiectasia, Canavan Disease, Cockayne Syndrome, Corticobasal Degeneration, Creutzfeldt-Jakob Disease, Huntington's Disease, Kennedy's Disease, Krabbe Disease, Lewy Body Dementia, Machado-Joseph Disease, Multiple Sclerosis, Parkinson's Disease, Pelizaeus-Merzbacher Disease, Niemann-Pick's Disease, Primary Lateral Sclerosis, Refsum's Disease, Sandhoff Disease, Schilder's Disease, Steele-Richardson-Olszewski Disease, or Tabes Dorsalis.
13. The method of paragraph 12, wherein the neurodegenerative disease or disorder is Parkinson's Diseases.
14. The method of paragraph 12, wherein the neurodegenerative disease or disorder is Alzheimer's Disease.
15. The method of paragraph 11, wherein the subject has a mental disorder.
16. The method of paragraph 15, wherein the mental disorder is depression or schizophrenia.
17. The method of paragraph 16, wherein the mental disorder is depression and the administering comprises administration of GD3 followed by administration of GM1.
18. The method of paragraph 16, wherein the mental disorder is schizophrenia and the administering comprises administration of GM1.
19. The method of paragraph 18, wherein administering comprises administration of GM1 and is free from administration of GD3.
20. The method of paragraph 11, wherein the subject comprises a disease or injury of the eye optionally comprises retinal injury or degeneration.
21. The method of paragraph 11, wherein the subject has suffered a traumatic brain injury.
22. The method of paragraph 11, wherein the subject suffers from olfactory impairment.
23. The method of any one of paragraphs 1-9, wherein the subject does not yet suffer from damage or deterioration of neurons.
24. The method of paragraph 23, wherein the subject is expected to or likely to develop damage or deterioration of neurons optionally because the subject has a genetic predisposition and/or familial history with a neurodegenerative, mental, or neuronal disease or disorder.
25. The method of any one of paragraphs 1-24, wherein the method reduces formation of or existing cytotoxic proteins amyloid β-peptide (Aβ) and alpha-synuclein (aSyn).
26. The method of any one of paragraphs 1-25, wherein the GD3 and/or GM1 are administered in an effective amount and for a sufficient duration to increase and/or restore neural stem cell activity and/or neurogenesis.
27. A method for treating neurodegeneration and/or injury to the eye(s) comprising administering an effective amount of ganglioside GD3 and/or ganglioside GM1 into the eye(s) of the subject.

28. The method of paragraph 27, wherein the ganglioside(s) are present in an ocular formulation selected from solutions, suspensions, ointments, creams, or solid inserts.

29. The method of paragraphs 27 and 28, wherein the ganglioside(s) are administered to the eyes using drops dispensed from an eye dropper.

30. The method of any one of paragraphs 27-29, wherein GD3 as administered in an effective amount to increase the number of neural stem cells (NSCs).

31. The method of any one of paragraphs 27-30, wherein GM1 is administered in an effective amount to increase neuronal differentiation.

32. The method of any one of paragraphs 27-29, wherein GD3 is administered prior to GM1.

33. The method of paragraph 32, wherein administration of the GM1 is after GD3 has begun increasing the number of NSCs, and wherein GM1 increases differentiation of the NSCs.

34. The method of any one of paragraphs 27-33, comprising two or more administrations for GD3 and/or GM1.

35. The method of any one of paragraphs 27-34 comprising concurrent, sequential and overlapping, and/or sequential and non-overlapping administration of GM1 and GD3.

36. The method of any one of paragraphs 27-29, 31 or 34, wherein GM1 is administered alone and in the absence of GD3.

37. The method of any one of paragraphs 27-30, or 34, wherein the GD3 is administered alone or in the absence of GM1.

38. The method of any one of paragraphs 27-37, wherein the neurodegeneration comprises damage or deterioration of neurons.

39. A dosage unit composition comprising an effective amount the ganglioside(s) according to the method of any one of paragraphs 1-38.

40 The dosage unit composition of paragraph 39 for use in the method of any one of paragraphs 1-38.

EXAMPLES

Itokazu, et al., "Intranasal infusion of GD3 and GM1 gangliosides downregulates alpha-synuclein and controls tyrosine hydroxylase gene in a PD model mouse", *Molecular Therapy*, VOLUME 29, ISSUE 10, P3059-3071, Oct. 6, 2021, is specifically incorporated by reference herein in its entirety.

Introduction

Figure 1B:
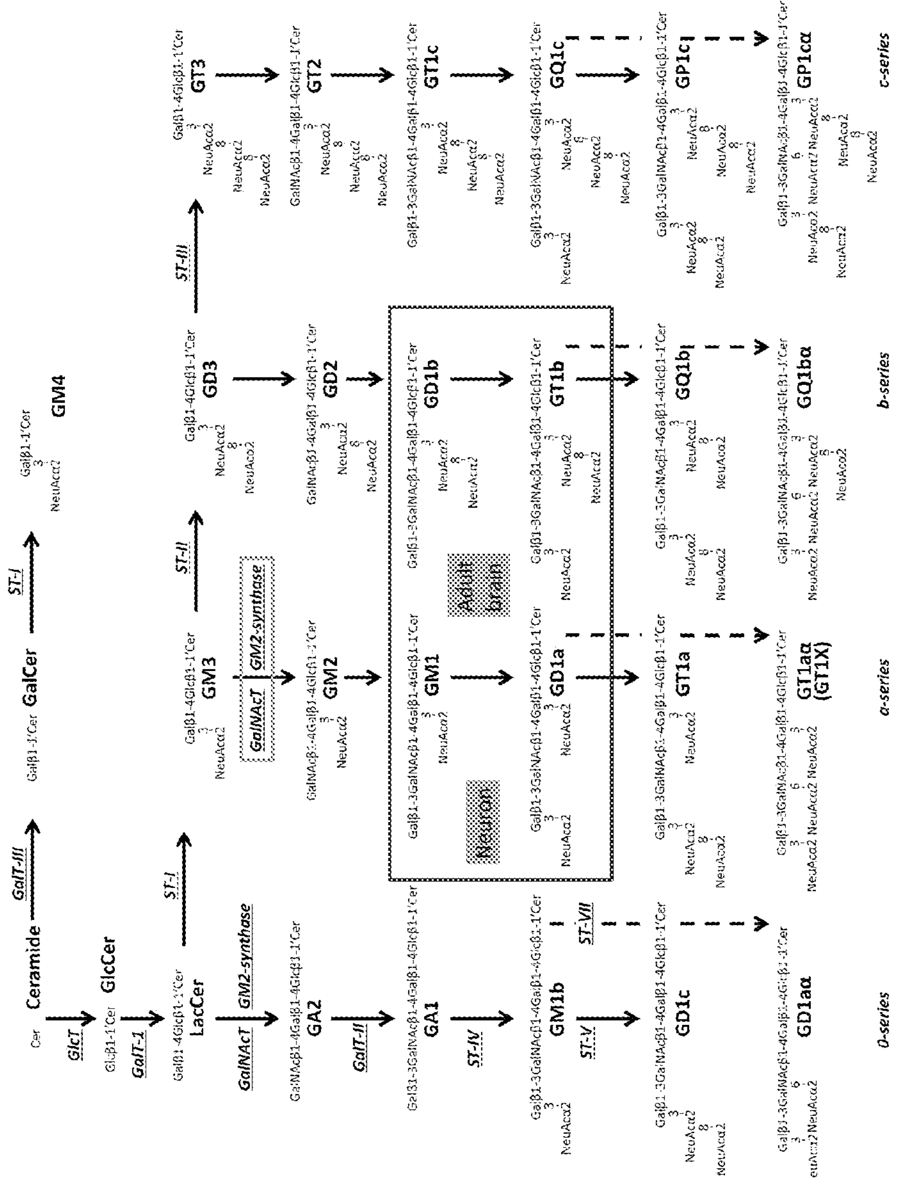
FIG. 1B is an illustration of metabolic pathways and structure of glycosphingolipids, including gangliosides. Cer, ceramide; GalNAc-T, N-acetylgalactosaminyltransferase I (B4galnt1, GA2/GM2/GD2/GT2 synthase); GalT-I, galactosyltransferase I (B4galt6, lactosylceramide synthase); GalT-II, galactosyltransferase II (B3galt4, GA1/GM1/GD1b/GT1c synthase); GalT-III, galactosyltransferase III (Ugt8a, galactosylceramide synthase); GlcT, gluco-syltransferase (Ugcg, glucosylceramide synthase); ST-I, sialyltransferase I (St3gal5, GM3/GM4 synthase); ST-II, sialyltransferase II (St8Sia1, GD3 synthase); ST-III, sialyl-transferase III (St8Sia3, GT3 synthase); ST-IV, sialyltransferase IV (St3gal2, GM1b/GD1a/GT1b/GQ1c synthase); ST-V, sialyltransferase V (St8sia5, GD1c/GT1a/GQ1b/GP1c synthase); ST-VII, sialyltransferase VII (St6galnac6, GD1aa/GT1aa/GQ1ba/GP1ca synthase). Official symbols of genes are represented in italics in this legend. GM1, GD1a, GD1b, and GT1b are the most abundant ganglioside species in adult mammalian brain and neurons.

The expression patterns of gangliosides change dramatically during brain development and cellular differentiation (Yu & Itokazu, *Advances in neurobiology,* 9:185-222. PubMed PMID: 25151380 (2014)) and are mainly regulated by glycosyltransferases (GTs). Changes in GT expression in NSCs rationalize the dramatic changes of ganglioside expression during differentiation. The synthesis of GD3 is switched into the synthesis of complex gangliosides (GM1, GD1a, GD1b, and GT1b: FIGS. 1A and 1B), resulting in terminal differentiation and loss of the "stemness" of NSCs.

GD3 interacts with epidermal growth factor receptor (EGFR), an important mitogen receptor for the self-renewal of NSCs in the glycolipid-enriched microdomains (GEMs)/lipid rafts of the plasma membrane. Further in vitro and in vivo experiments showed that this interaction functions as: 1) a "platform" to initiate EGFR downstream signaling to induce NSC self-renewal; and 2) a "director" for the recycling of EGFR after endocytosis. In this way, the self-renewal capacity of NSCs is maintained with continuous mitogen stimulation with GD3 (Yu & Itokazu, *Advances in neurobiology,* 9:185-222. PubMed PMID: 25151380 (2014), Wang & Yu RK, *Proceedings of the National Academy of Sciences of the United States of America,* 110(47):19137-42. PubMed PMID: 24198336. Pubmed Central PMCID: 3839736 (2013)), and GD3 plays a role in the long-term maintenance of NSC populations in the dentate gyms (DG) of hippocampus and subventricular zone (SVZ) of postnatal mouse brain (Wang et al., *The Journal of neuroscience: the official journal of the Society for Neuroscience.* 34 (41): 13790-800. PubMed PMID: 25297105. Pubmed Central PMCID: 4188974 (2014)). Moreover, the impaired neurogenesis in the adult GD3S-KO mice led to depression-like behaviors. These results link ganglioside deficiency to behavioral deficits, and support a role of gangliosides in the long-term maintenance of adult neurogenesis.

GD3S-KO mice tested using the Barnes maze task, a widely used test of hippocampal-dependent spatial memory, displayed a significant spatial memory deficit as evidenced by an increase in escape latency to find the hidden chamber on the third day of the training trial, with decreased quadrant occupancy and increased number of exploring errors on probe trial compared with wild-type (WT) mice. In line with this, using the object recognition test, loss of GD3 was shown to impair hippocampal-dependent recognition memory, as evidenced by a significant decrease in preference to explore new objects compared with the WT mice. These findings are consistent with the conclusion that GD3 has an important role in hippocampal-dependent learning and memory (Tang et al., *J Neurochem*, PubMed PMID: 32743804. Epub 2020 Aug. 4 (2020)).

Whether integration of adult-born neurons into the existing circuitry would be impaired in the absence of GD3 was also explored. A retrovirus encoding for GFP (CAG-GFP) was stereotactically injected into the DG of 2-month-old GD3S-KO and WT mice Animals were sacrificed at 14, 28, and 42 days post-retrovirus injection (dpi). The dendritic complexity of GD3S-deficient neurons was reduced at sites more than 50 μm from the soma compared with control neurons at 42 dpi. Dendrite development of adult-born neurons in the DG of adult hippocampus is important for their incorporation into existing hippocampal circuits, but the cellular mechanisms regulating dendrite development remains largely unclear. Results show that GD3 plays an important role in regulating dendrite morphogenesis, and that spine density of GD3S-KO neurons was reduced. 3D-analysis of spine morphology showed that GD3S-KO neurons had fewer mature spines (so called mushroom spines). These data indicate that GD3 is important to control dendrite and spine development. GD3 is important for the developing of the adult-born neurons to control dendrite and spine maturations in the hippocampus (Tang et al., *J Neurochem*, PubMed PMID: 32743804. Epub 2020 Aug. 4 (2020)).

GEMs/lipid rafts on the plasma membrane surface are generally accepted as an important site for signal transduction. Nuclear lipid domains on the nuclear envelope have also recently been proposed to play a similar role. GM1 and GD1a (FIGS. 1A and 1B) have been detected in the inner and outer nuclear membranes. The nuclear distribution of gangliosides in the developing brain reflects their composition in the whole brain (Yu & Itokazu, *Advances in neurobiology,* 9:185-222. PubMed PMID: 25151380 (2014), Itokazu et al., *Progress in molecular biology and translational science,* 156:241-63. PubMed PMID: 29747816. Pubmed Central PMCID: 6261283 (2018)). With regard to gangliosides association with chromatins, GD3 is reported to interact with histone H1 in the nucleus.

Figure 2B:
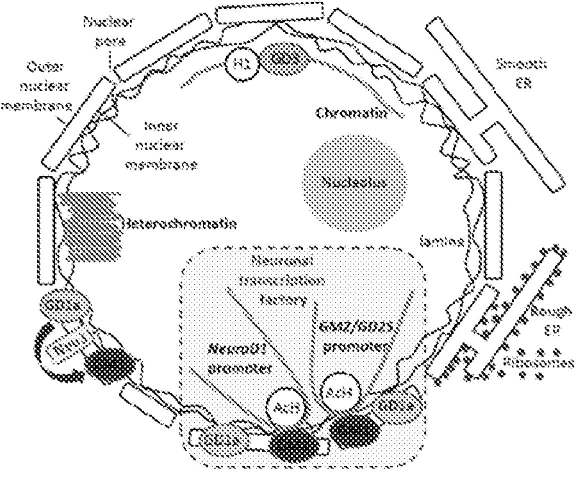
FIG. 2B is a model of epigenetic regulation by gangliosides. A model depicting the regulation of glycosyltransferase GM2S (GalNAcT; B4galnt1) gene by GM1 for neuronal differentiation. GM1 and its metabolic precursor GD1a exist on nuclear membrane. GM1 interacts with acetylated histones (AcH) which are active epigenetic marks. GM1 binds with GM2S and NeuroD1genes, and GM1 enhances histone acetylation on the promoters of the GM2S as well as on the NeuroD1 genes in differentiated neurons. These associations of GM1 and these genes were found in differentiated neurons, but not in NSCs. The interaction of GM1 and the GM2S gene promoter occurs in a differentiation stage-specific manner At a later differentiation stage, the nuclear GM1-lipid domains may serve as a docking site at the nuclear periphery for specific active chromatins for neuronal differentiation. Neu3: sialidase 3.

It has also been shown that nuclear sphingolipids participate in epigenetic regulation of gene expression by controlling histone acetylation. Nuclear membrane glycolipids, in particular gangliosides, may contribute, in a stage- and cell-specific manner, to modulate gene expression as happening on the nuclear membrane. The nuclear envelope, including the nuclear lamina and nuclear pore complexes, is a key structure to maintain chromatin architecture and cell-specific gene expression. GM1 interacts with both the GM2 synthase (GM2S) and NeuroD1 promoter regions, and GM1 also interacts with acetylated histones. The nuclear GEMs/lipid rafts may modulate gene transcription during neural cell differentiation and in pathogenetic mechanisms of a number of neurodegenerative diseases (FIG. 2B) (Tsai & Yu, *J Neurochem,* 128(1):101-10. PubMed PMID: 24102378 (2014), Tsai et al., *Neurochemical research,* 41(1-2):107-15. PubMed PMID: 26498762. Pubmed Central PMCID: 4775412 (2016), Itokazu et al., *Glycoconjugate journal*, PubMed PMID: 27540730 (2016)). Data supports that gangliosides themselves can modulate epigenetic gene expression, presumably by a feed-back mechanism.

As introduced above, GD3S-KO mice show reduced NSC pool (Wang et al., *The Journal of neuroscience: the official journal of the Society for Neuroscience.* 34 (41):13790-800. PubMed PMID: 25297105. Pubmed Central PMCID: 4188974 (2014)) and impaired hippocampal memory functions (Tang et al., *J Neurochem*, PubMed PMID: 32743804. Epub 2020 Aug. 4 (2020)). The functional roles of GD3 in postnatal NSCs in DG and SVZ were also investigated. GD3 and GM1 were isolated from either bovine buttermilk or brains by established procedures (Itokazu, Yutaka et al. *ASN neuro.,* 11: 1759091419884859 (2019) incorporated herein by reference). GD3 was added back into the neurogenic region of GD3S-KO mouse via icv for 7 days by micro-osmotic pump (5 mg/kg/day). Results show that icv infusion of GD3 augments NSC pools in DG and SVZ of the adult mouse brain (Itokazu et al., *ASN neuro,* 11:1759091419884859. PubMed PMID: 31635474. Pubmed Central PMCID: 6806120 (2019)).

The 5XFAD transgenic mice have severe pathological phenotypes with two-point mutations in PSEN1 (M146L & L286V) and the Florida (I716V), London (V717I), and Swedish (KM670/671NL) mutations in APP. To examine the physiological roles of GD3 and GM1 on postnatal neurogenesis in the brain of AD model mice, gangliosides (GD3 or GM1 and combination; 5 mg/kg/day for 7 days) were icv administrated into the 5XFAD mouse brain. Results show that GD3 augments self-renewal and multipotent marker, SOX2-expressing cells in DG10. On the other hand, GM1 increases BrdU+/doublecortin+ (DCX+) newly generated immature neurons in 5XFAD mouse brains.

Materials and Methods

Experimental Models

The GD3 synthase-knockout (GD3S KO) mouse model is biologically representative of human of Alzheimer's disease. Impaired neurogenesis in the adult GD3S-KO mice has been shown to lead to depression-like behaviors, providing direct evidence linking ganglioside deficiency to behavioral deficits, and support a crucial role of gangliosides in the long-term maintenance of adult neurogenesis. (Wang, J. et al., The Journal of Neuroscience: the official journal of the Society for Neuroscience. 34 (41):13790-800 (2014)).

The 5xFAD mouse model is widely used to recapitulate many Alzheimer's disease-related phenotypes and has a relatively early and aggressive presentation. Amyloid plaques, accompanied by gliosis, are seen in mice as young as two months of age. Amyloid pathology is more severe in females than in males. Neuron loss occurs in multiple brain regions, beginning at about 6 months in the areas with the most pronounced amyloidosis. Mice display a range of cognitive and motor deficits.

The Hualpha-Syn (A53T) transgenic mouse line G2-3 is biologically representative of human Parkinson's disease and is often used to study other synucleinopathies associated with motor neuron loss and ubiquitinated inclusions in the brain stem and the spinal cord, Lewy bodies, and synaptic plasticity.

All animal experiments were performed with animal protocols (references AUP 2009-0240 and 2014-0694) approved by the Institutional Animal Care and Use Committee (IACUC) at Augusta University (AU) according to the National Institutes of Health (NIH) guidelines Animal protocols were approved for the described mice. For the PD model, mice expressing A53T mutant human aSyn under the murine prion promoter were utilized. This mouse line (B6.Cg-2310039L15RikTg(Prnp-SNCA*A53T)23Mkle/J) (The Jackson Laboratory, Bar Harbor, ME, USA, stock no 006823) is referred to as the A53T PD mouse. C57B6/6 mice were obtained from The Jackson Laboratory (stock no. 000664). For GM2S-KO mice, the original GM2S-KO mice (GM2 synthase KO, B4galnt1-KO, B6; 1295-B4galnt1tm1R1p/Mmmh) (MMRRC stock no. 000036-MU) and their WT mates were crossed to generate the heterozygous mice. Then, the heterozygous male and female mice were mated, and PCR screening was performed for genotyping. Littermates were used as controls. All mice were housed in standard conditions with food and water provided ad libitum and maintained on a 12-h dark/12-h light cycle.

Mouse Neuro-2a neuroblastoma cells (ATCC, Manassas, VA, USA, CCL-131) were maintained in Dulbecco's modified Eagle's medium supplemented with 10% fetal bovine serum, 2 mM glutamine, and penicillin/streptomycin at 37° C., 5% CO2.

Antibodies

Mouse anti-aSyn (BD Biosciences, San Jose, CA, USA, 610787), rabbit anti-phospho-S129 aSyn (Abcam, Cambridge, MA, USA, ab51253), rabbit anti-TH (Millipore, St. Louis, MO, USA, AB152), mouse anti-TH (Invitrogen from Thermo Fisher Scientific, Rockford IL, USA, MA5-35009), goat anti-Nurr1 (R&D Systems, Minneapolis, MN, USA, AF2156), mouse anti-lamin B1 (Abcam, ab20396), rabbit anti-lamin B1 (Abcam, ab16048), rabbit anti-VDAC1 (Cell Signaling Technology, Danvers, MA, USA, D73D12), mouse anti-GM1 (TCI America, Portland, OR, USA, A2505), rabbit anti-actin (Sigma, St. Louis, MO, USA, A2066), rabbit anti-acetylated histone H3 (Milli-pore, 06-599), rabbit anti-PITX3 (Thermo Fisher Scientific, 382850), Alexa Fluor 488-conjugated goat anti-mouse immunoglobulin G (IgG) (Invitrogen, A28175), Alexa Fluor 488-conjugated goat anti-rabbit IgG (Invitrogen, A11008), Alexa Fluor 568-conjugated goat anti-rabbit IgG (Invitrogen, A11011), Alexa Fluor 647-conjugated goat anti-rabbit IgG (Invitrogen, A27040), Alexa Fluor 488-conjugated donkey anti-rabbit IgG (Invitrogen, R37118), Alexa Fluor 488-conjugated donkey anti-mouse IgG (Invitrogen, R37114), anti-mouse IgG-horseradish peroxidase (HRP) (Thermo Fisher Scientific, 45000692), and anti-rabbit IgG-HRP (Sigma-Aldrich, GENA934) antibodies were purchased.

Intranasal Ganglioside Infusion

The acquisition, care, and experimental treatment of animals used in this study were in compliance with the NIH guidelines as published in the Guide for the Care and Use of Laboratory Animals. Gangliosides (GD3 or GM1; 5 mg/kg/day) were infused intranasally (Hanson, et al., *J. Vis. Exp.* (74) (2013) doi.org/10.3791/4440.) with a small pipette (each 6 mL into the right and left nares twice, or 24 mL per day) into 8-month-old WT (C57B6/J), A53T PD, and GM2S-KO mice daily for 7-28 days. GD3 and GM1 used in this study were isolated from either bovine buttermilk or brains by established procedures (Ariga, et al., J. Biol. Chem. 269, 2667-2675 (1994), Ledeen and Yu, Methods Enzymol. 83, 139-191 (1982), Ren, et al., J. Biol. Chem. 267, 12632-12638 (1992)). Gangliosides, being amphipathic, were easily dissolved in saline. The placebo group received saline infusions. At first, to provide direct evidence for ganglioside administration into brain, mice totally deficient in GM1 (8-month-old GM2S-KO mice) were intranasally administered GM1 (0.5 or 5 mg/kg/day) for 7 days. Brain-delivered GM1 was analyzed by immunohistochemistry and TLC. After confirmation that ganglioside reached the brain of GM2S-KO mice by the intranasal route, 8-month-old A53T PD mice were utilized for ganglioside treatments (28 days). Animals were divided into five groups: (1) a WT with saline infusion group; (2) a A53T PD with saline infusion group; (3) a A53T PD with GD3 (5 mg/kg/day) infusion group; (4) a A53T PD with GM1 (5 mg/kg/day) infusion group; and (5) a GD3 infusion plus GM1 infusion group (GD3 at 5 mg/kg/day for 14 days, then GM1 at 5 mg/kg/day for the other 14 days). Each group consisted of n=3-4 animals. Also, 5 mg/kg/day GM1 was intranasally administered to GM2S-KO mice for 28 days to analyze TH expression.

Immunohistochemistry

Mice were transcardially perfused with phosphate-buffered saline (PBS, pH 7.4) and 4% paraformaldehyde (PFA). The brains were removed and post-fixed with the same fixative overnight, followed by cryoprotection with 30% sucrose in PBS, and the solution was changed more than three times, at 4° C. After embedding in Tissue-Tek OCT compound (Sakura Finetek, Torrance, CA, USA), the brains were quickly frozen in liquid nitrogen. Cryosectioning was performed (20-mm-thick sections) using a cryostat (Leica, Wetzlar, Germany). For co-staining of GM1 and TH, sections were permeabilized with PBS containing 0.5% Triton X-100 for 5 min, followed by blocking with PBS containing 1% bovine serum albumin (BSA) for 30 min at room temperature, and then incubated with Alexa Fluor 594-conjugated cholera toxin B subunit (CtxB) (1:5,000, Invitrogen, C22842) and rabbit anti-TH antibody (1:500, Millipore, AB152) overnight. For co-immunostaining aSyn and phospho-S129 aSyn or lamin B1, antigen retrieval was performed by autoclave treatment in 10 mM citrate buffer (pH 3.0) at 121° C. for 25 min, followed by permeabilization and blocking as described above. Then, sections were subjected to reaction with mouse anti-aSyn antibody (1:100, BD Biosciences, 610787) and rabbit anti-phospho-S129 aSyn antibody (1:100, Abcam, ab51253) or rabbit anti-lamin B1 antibody (1:100, Abcam, ab16048). For staining VDAC1 or co-staining Nurr1 and TH, microwave treatment was performed in pre-boiled 10 mM citrate buffer (pH 6.0) for 5 min, followed by incubation with rabbit anti-VDAC1 antibody (1:100, Cell Signaling Technology, D73D12) and mouse anti-TH anti-body (1:100, Invitrogen, MA5-35009), or goat anti-Nurr1 antibody (1:100, R&D Systems, AF2156) and rabbit anti-TH antibody (1:500, Millipore, AB152). Each reaction with primary antibodies was followed by incubation with Alexa Fluor-conjugated secondary antibody for 2 h at room temperature, and then nuclei counterstaining was performed with 1 mg/mL 40,6-diamidino-2-phenylindole (DAPI) (Thermo Fisher Scientific, D1306) for 30 min. After every incubation with antibodies or chemicals, sections were washed three times with PBS. Specimens were mounted with VectaMount (Vector Laboratories, Burlingame, CA, USA).

Microscopy and Image Processing

Confocal images were acquired using a Zeiss LSM 700 with a ×63 oil objective (Zeiss, Land Baden-Württemberg, Germany) with identical acquisition settings. Zen software was used for initial image acquisition of the fluorescent signals. Quantitative analyses of digital images were performed using Fiji (NIH, Bethesda, MD, USA). Serial z axis images were converted into stacks, and average intensities were measured within the indicative aSyn-, TH-, and Nurr1-stained subcellular or nuclear area (n=3-4 mice, 7-12 regions per each condition). To generate unbiased data, the blinding procedures and randomized field approach for images were performed.

Ganglioside Isolation and TLC

Gangliosides were isolated from cortical tissue from WT and GM2S-KO mice as previously described 73 with some modifications. 74 Briefly, total lipids were extracted from brain tissues with chloroform-methanol-water (30:60:8 [v/v]; solvent A) after cardio-vascular perfusion with PBS. Then, the extracts were evaporated and dissolved in 1 mL of solvent A and applied to a diethylami-noethyl (DEAE)-Sephadex A-25 column (acetate form, 1-mL bed volume), followed by elution with 10 mL of solvent A to remove the neutral lipids. The acidic lipid fraction, containing gangliosides, was then eluted with 10 mL of chloroform-methanol-0.8 M sodium acetate in water (30:60:8 [v/v]; solvent B), followed by desalting using Sep-Pak cartridge column chromatography (Waters, Milford, MA, USA).75 Gangliosides were applied to a high-performance TLC (HPTLC, aluminum HPTLC silica gel; Merck, Darmstadt, Germany) plate and developed with the solvent system of chloroform-methanol-water containing 0.2% $CaC_{12}/H_2O$ (50:45:10 [v/v]). After developing the HPTLC plate described above, the plate was coated in a solution of n-hexane containing 0.02% poly(isobutyl methacrylate) for 1 min. After drying, the plate was then incubated in blocking buffer (1% BSA/1% polyvinylpyrrolidine) at room temperature for 30 min. Staining of GM1 on TLC plates was performed using a protocol for immunostaining of lipids except that HRP-labeled CtxB (Invitrogen, C34780) was used instead of antibodies. 64 Plates were rinsed with washing buffer (PBS/1% Tween 20) and incubated with CtxB-HRP at 4° C. overnight. After washing with washing buffer, signals were visualized with enhanced chemiluminescence reagent (PerkinElmer Life and Analytical Sciences, Boston, MA, USA).

Western Blotting

The entire substantia nigra region was isolated by dissection under a SZX7 stereo microscope (Olympus, Tokyo, Japan). Tissue blocks were lysed in radioimmunoprecipitation assay (RIPA) buffer containing 50 mM Tris-HCl, 150 mM NaCl, 5 mM NaF, 1 mM Na3VO4, 1% Nonidet P-40 (NP-40), 0.5% sodium deoxycholate, and 1% SDS (pH 7.5), supplemented with a complete protease inhibitor cocktail (Roche Applied Science, Indianapolis, IN, USA). The protein concentrations were measured using a bicinchoninic acid protein assay kit (Thermo Fisher Scientific, Rockford IL, USA). Proteins (10 mg) were separated by SDS-PAGE (10% gel) under reducing conditions and transferred to polyvinylidene fluoride (PVDF) membranes. The membranes were probed with primary antibodies for aSyn, phospho-S129 aSyn, VDAC1, and actin, followed by appropriate secondary antibodies conjugated with HRP. Signals were visualized with Western Lightning western blot chemiluminescence reagent (PerkinElmer Life and Analytical Sciences, Waltham, MA, USA).

Gene Expression Analysis by qPCR

Total RNA samples were isolated from substantia nigra of mouse brains or cultured Neuro 2a cells using TRIzol reagent (Life Technologies from Thermo Fisher Scientific). Neuro 2a cells were untreated or treated with 5 mM GD3 or GM1 in B27-supplemented Neuro-basal-A medium for 24 h. cDNAs were synthesized based on the total RNAs as templates using MultiScribe reverse transcriptase (Applied Biosystems, Waltham, MA, USA). qPCR was performed with run RT2 SYBR Green qPCR master mix (QIAGEN, Hilden, Germany) on the CFX96 system (Bio-Rad, Hercules, CA, USA). The relative expression levels of TH were normalized to the actin transcript level. The normalized value from control (WT+saline, or no treated cells) is defined as 1.0. The following primers were used: TH forward, 5'-CACTATGCCCACCCCCAG-3' (SEQ ID NO:1), reverse: 5'-CGCCGTCCAATGAACCTT-3' (SEQ ID NO:2); actin forward, 5'-CTAAGGCCAACCGTGAAAAGAT-3' (SEQ ID NO:3), reverse, 5'-CACAGCCTGGATGGCTACGT-3' (SEQ ID NO:4).

ChIP Assay

ChIP assays were performed on cell lysates as previously described.31,32,76 Briefly, Neuro 2a cells, untreated or treated with 5 mM GD3 or GM1 for 24 h, were incubated in 1% PFA for 10 min at ambient temperature to crosslink the interacting partners. Cells with the cross-linked complexes were subjected to lysis by sonication with six 20-s pulses at the power scale 7 controlled by a sonicator (Sonic dismembrator model 100, Fisher Scientific). After centrifugation at 15,000×g for 10 min, the supernatants were collected for the following experiments. Immunoprecipitation was carried out with the following specific antibodies bound on protein G-conjugated magnetic beads (Millipore): anti-acetylated histone H3 (Millipore), anti-Nurr1 (R&D Systems), or anti-PITX3 (Thermo Fisher Scientific) antibodies. The amounts of the co-precipitated DNA fragments of TH promoter (+0), the Nurr1 binding site on the TH promoter (TH-NBS), and the PITX3 binding site on TH promoter (TH-PBS) were analyzed by qPCR. After normalization against GAPDH, the value of no treated cells was defined as 1.0. The following primers were used: TH forward, 5'-TAAGAGGCCGCCTGCCTGGC-3' (SEQ ID NO:5), reverse, 5'-GTCTCGTCCTATGGTTCGTC-3' (SEQ ID NO:6); TH NBS forward, 5'-TCCAGGAGAACAGACGCCAGC-3' (SEQ ID NO:7), reverse, 5'-GCCAGGCTGAAGGCAAGCACA-3' (SEQ ID NO:8); TH PBS forward, 5'-TTCCATGAAAGCACAACTGGC-3' (SEQ ID NO:9), reverse, 5'-CAGGGTCGGCTGCTGAGGAT-3' (SEQ ID NO:10); GAPDH forward, 5'-ACCAGGGAGGGCTGCAGTCC-3' (SEQ ID NO:11), reverse, 5'-TCAGTTCGGAG CCCACACGC-3' (SEQ ID NO:12).

Photoclick GM1 and Isolation of Nuclei from Cultured Cells

Cells were incubated with 1 mM pacGM1 (Avanti Polar Lipids, Birmingham, AL, USA, 900603) for 24 h. Cells were UV irradiated at 365 nm for 30 min on ice. Nuclei were isolated using modification of previously described procedures.77,78 The scraped cells in ice-cold PBS were pelleted at 250×g, 4° C. for 5 min. The pellets were suspended in 300 mL of TM buffer (20 mM Tris-Cl [pH 7.5], 1 mM MgCl2) supplemented with 0.1% Triton X-100 and incubated on ice for 30 min. Nuclei were recovered by centrifugation at 800×g, 4° C. The pellet was homogenized in 2 M sucrose in TM buffer and centrifuged at 100,000×g, 4° C. for 25 mM To minimize contamination by other subcellular organelles, the ultracentrifuged pellet was homogenized in 0.32 M sucrose in TM buffer, overlaid on 2.2 M sucrose in TM buffer, and recentrifuged as before. The isolated nuclei were placed on poly-D-lysine-coated glass slides and fixed in 4% PFA in PBS for 20 mM at room temperature. Nuclei were washed with PBS, and the click reaction was performed using the Invitrogen Click-iT cell reaction buffer kit (Thermo Fisher Scientific, C10269) using TAMRA (carboxytetramethylrhodamine)-azide-desthiobiotin (Click Chemistry Tools, Scottsdale, AZ, USA, 1110-5) as fluorophores following the manufacturers' protocols. Zeiss LSM 700 confocal microscopy was performed as described above (see Microscopy and image processing).

PLAs on Purified Nuclei of Adult Mouse Brain

Nuclei were isolated from WT mouse cerebrum (8-month-old mice) using modification of previously described procedures. 77,79 Brain tissue was homogenized in 1.3 M sucrose in TM buffer, and the homogenate was centrifuged at 100,000×g, 4° C. for 25 min. The ultracentrifuged pellet was homogenized in 0.32 M sucrose in TM buffer, overlaid on 2.2 M sucrose in TM buffer, and recentrifuged as before. The isolated nuclei were fixed on cover glass as described above. Nonspecific binding sites were blocked with Duolink PLA blocking solution for 1 h at 37° C. The primary antibodies used were mouse anti-GM1 (1:100) and rabbit anti-acetylated histone H3 (1:100). Secondary PLA probes were anti-rabbit PLUS affinity-purified donkey anti-rabbit IgG (H+L) and anti-mouse MINUS affinity-purified donkey anti-mouse IgG (H+L), which were diluted 1:5 in 1× anti-body diluent buffer and samples were incubated for 1 h at 37° C. After washing, ligation and amplification steps were performed following the manufacturer's protocol. Zeiss LSM 700 confocal microscopy was performed as above (see Microscopy and image processing). A PLA Duolink in situ red starter kit mouse/rabbit was purchased from MilliporeSigma (DU092101).

Statistical Analysis

All statistical procedures were performed using GraphPad Prism 9 (GraphPad, San Diego, CA, USA). Normality and homogeneity of variances of datasets were checked by a Kolmogorov-Smirnov test and Brown-Forsythe test, respectively. When datasets passed these tests, a one-way ANOVA with a Tukey's multiple comparison test was performed. In all cases, p values are shown in the figure legends, and $p<0.05$ was regarded as significant. All graphs depict mean±SEM.

Results

Example 1: Intranasal Administration of Gangliosides into Mouse Brain

Figure 3:
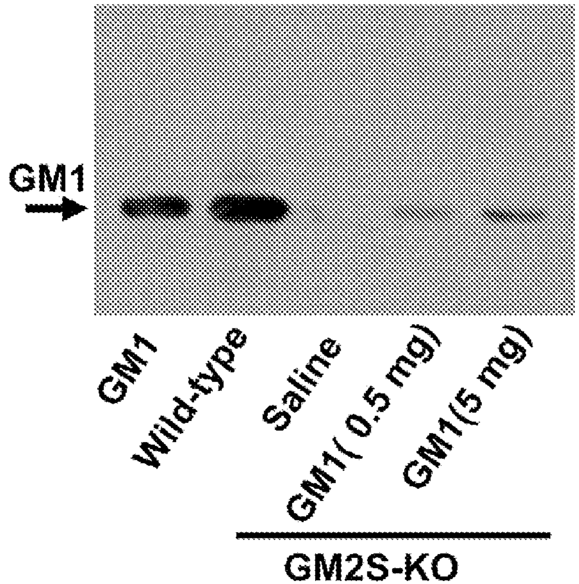
FIG. 3 is an image of blot showing intranasally administrated ganglioside was delivered to mouse brain. GM1 (0.5 mg/kg/day or 5 mg/kg/day was injected into GM2S-KO (GM1-KO) mouse for 7 days. GM1 bands on TLC were visualized with cholera toxin B-HRP. Microscopy also revealed that intranasally infused GM1 (5 mg/kg/day) could be delivered to cortical tissue and substantia nigra in the midbrain of GM1-KO mouse.

Historically, icv administration is the most reliable method to deliver gangliosides into the brain. Disclosed herein is a more convenient noninvasive delivery procedure by intranasal infusion of gangliosides with success. Ganglioside (GM1; 5 mg/kg/day) was injected by intranasally with small pipet (6 μl×4 times=24 ul per day) into 6-7-month-old GM2S-KO mice for daily for 1 week (Hanson, et al., *JoVE*. (74) (2013). PubMed PMID: 23608783. Pubmed Central PMCID: 3653240.). Mice lacking GM2S do not express GalNAc-containing gangliosides, including GM1 (FIGS. 1A and 1B). Gangliosides (about 4-10 mg/ml) were dissolved in saline. If the weight of a mouse is 20 g, 4.17 mg/ml of ganglioside in saline was prepared. Gangliosides is easily dissolved in saline. The placebo group received a saline infusion. Intranasally administrated gangliosides were successfully delivered to brain tissue including olfactory bulb subventricular zone, hippocampus, midbrain, cortex, and cerebellum (FIG. 3).

Figure 4A:
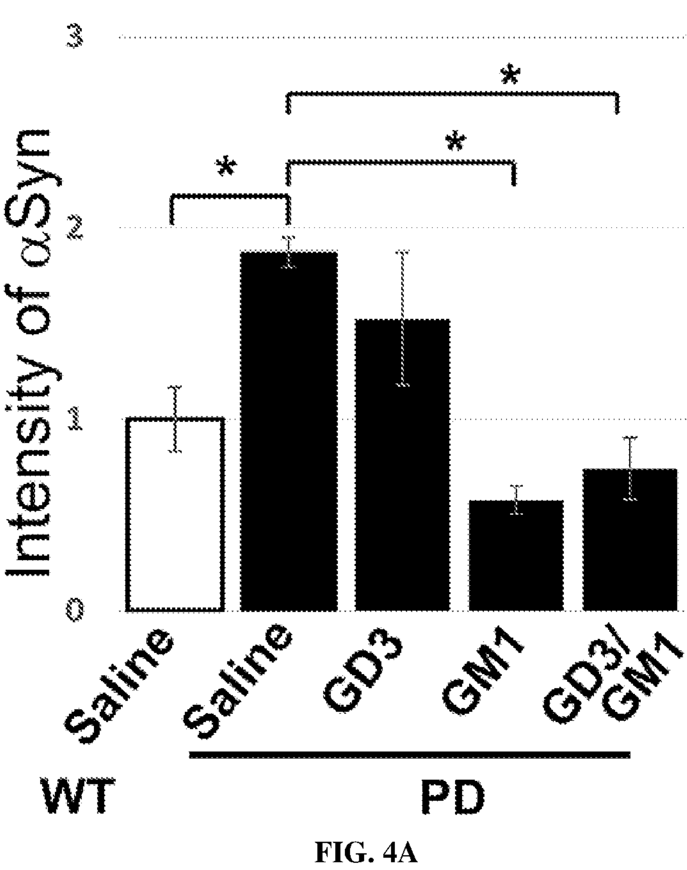
FIGS. 4A-4C show intranasally administrated gangliosides eliminate neurotoxic aSyn in PD mouse brain. Intranasally injected gangliosides (5 mg/kg/day for 28 days) removed aSyn and phospho-aSyn in PD mouse brain.
Figure 4B:
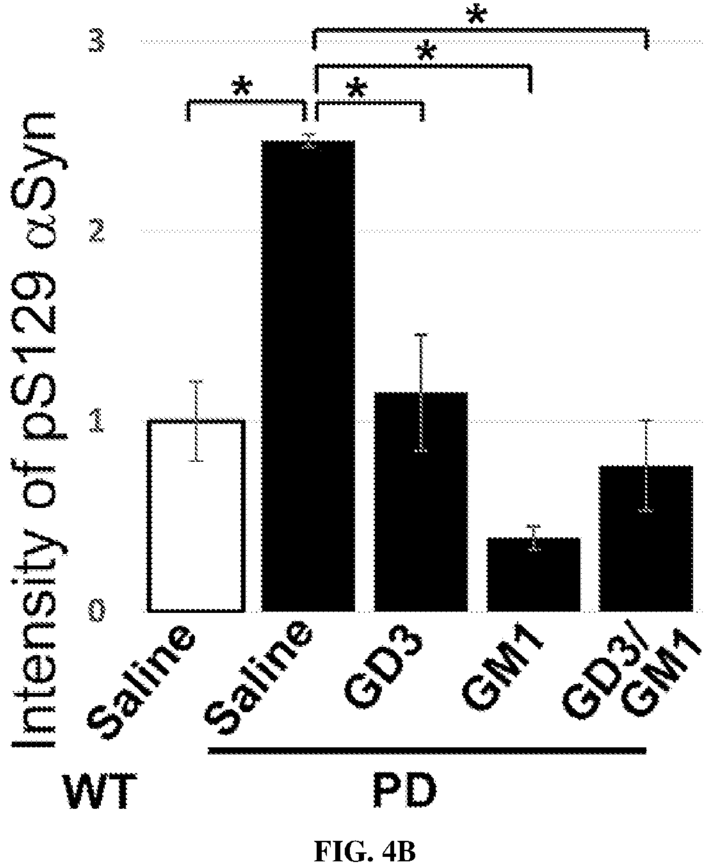
Figure 4C:
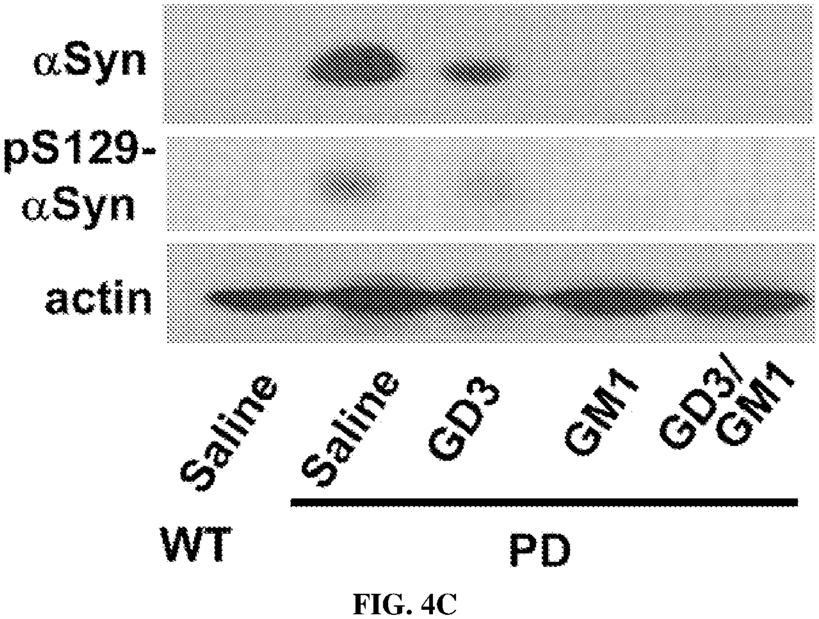

Example 2: Intranasally Administrated Gangliosides Eliminate Neurotoxic Proteins (aSyn) in PD Mouse Brain PD is a progressive neurodegenerative movement disorder affecting the body and mind of millions of people in the US. The number of patients is increasing. Two major pathological hallmarks of PD are aggregation of neurotoxic aSyn and loss of dopaminergic neurons. A PD model mice, which is known as Hualpha-Syn(A53T) transgenic line G2-3, was utilized. This transgenic mouse model displays an age-dependent phenotype including progressive motor deficits, intraneuronal inclusion bodies and neuronal loss. This line is widely used for studying PD and synucleinopathies. Gangliosides (5 mg/kg/day), GD3, GM1, or GD3-GM1 (GD3 for 2 weeks and GM1 for 2 week) into 8-month-old PD mice for 4 weeks (FIG. 4A-FIG. 8E). Intranasal administration of gangliosides dramatically reduced aSyn levels in PD brains (FIGS. 4A, 4C). Accumulation of aSyn phosphorylation at serine 129 has been reported in the brain of patients suffering from PD. Intranasal ganglioside administration also eliminated phosphorylated aSyn levels in PD mouse brains (FIGS. 4B, 4C). The results show that ganglioside can be a scavenger of neurotoxic proteins such as aSyn.

Example 3: Intranasally Administrated GM1 Increases Dopaminergic Neurons in PD Mouse Brain PD is a neurodegenerative disease characterized by the loss of midbrain dopamine neurons with a subsequent decrease in the concentration of striatal dopamine. Currently the only effective intervention of the disease symptoms of PD is based on treatment with the dopamine precursor L-DOPA. However, this treatment is only effective in the earlier stages of the disease. As the disease progresses, it shows reduced efficacy with the development of side effects, such as motor complications, in later stages. For this reason, it would be desirable to develop alternative strategies, such as dopamine neuron augmentation. Tyrosine hydroxylase (TH) is the rate-limiting enzyme in the synthesis of dopamine Expression level of TH is markedly reduced at substantia nigra in PD mouse brain (FIG. 5A) and intranasally infused ganglioside GM1 dramatically restored TH expression in PD mouse. This result shows GM1 protect dopaminergic neurons from PD brain.

Figures 5A, 5B:
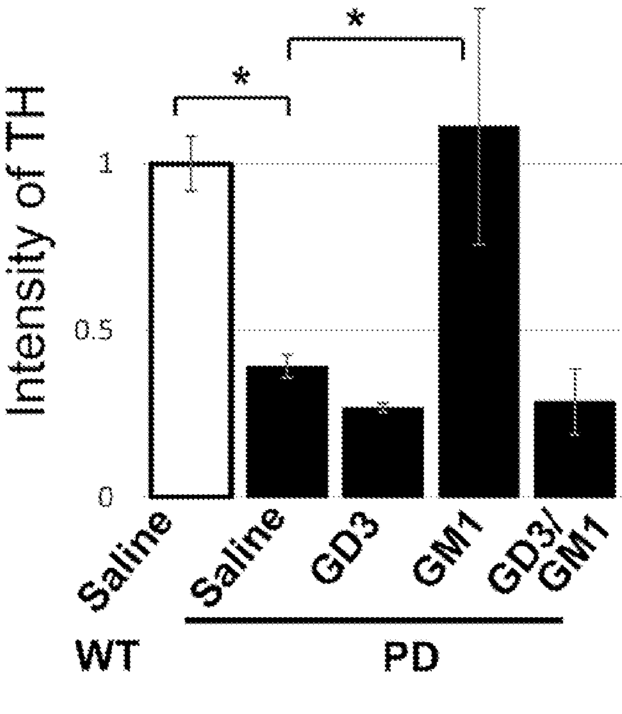
FIGS. 5A and 5B are bar graphs showing show intranasally administrated GM1 restored dopaminergic neurons in PD mouse brain. TH is the rate-limiting enzyme in the biosynthesis of dopamine, and it is regularly used as a marker for dopaminergic neurons. The transcription factor Nurr1 is important in the development and maintenance of dopaminergic neurons, and Nurr1 is associated with PD. Intranasal injected GM1 (5 mg/kg/day for 28 days) increased tyrosine hydroxylase (TH) expression at substantia nigra in PD mouse brain.

This result indicates that GM1 protects dopaminergic neurons from the cytotoxicity of aSyn in PD brain. Intriguingly, the expression and nuclear localization of Nurr1, a dopaminergic neuron-associated transcription factor involved in the expression of TH, were restored by intranasal administration of GM1 in the substantia nigra pars compacta of A53T PD mouse brains (FIG. 5B). These findings indicate that GM1 may participate in regulating the expression of TH by modulating Nurr1 activity.

Example 4: Intranasally Administrated Gangliosides Enhance Mitochondria Activity in PD Mouse Brain The mitochondria are the main intracellular organelle for producing adenosine triphosphate (ATP). PD was primarily regarded as a disease of dopaminergic neurons of the substantia nigra in which mitochondrial dysfunction.

Disruption of homeostasis and mitochondrial dysfunction play a very vital role in the pathogenesis of neurodegenerative diseases. A major component of the outer mitochondrial membrane, voltage-dependent anion channel 1 (VDAC1) known to regulate mitochondrial functions, is drastically down-regulated in PD mouse brain (FIG. 6). Intranasal-ganglioside administration dramatically restored VDAC1 levels in PD brain (FIG. 6). Intranasal administrated GD3 and GM1 significantly enhance the expression of this mitochondrial marker.

Example 5: Intranasal GD3 Increases NSC Number and GM1 Promotes Expression of Neuronal Ganglioside Synthase in PD Mouse Brain Patients with neurodegenerative diseases are suffering from cognitive impairment, depression, anxiety, and olfactory dysfunctions. These symptoms are believed to link with adult neurogenesis. GD3 is important to maintain memory function and GD3 deficient exhibit depressive symptoms with impaired postnatal neurogenesis. Intriguingly, intranasally administrated GD3 partially restored hippocampal NSC (Sox2 positive cell) number and combination of GD3 and GM1 (GD3 for 2 weeks and GM1 for 2 week) injection could restored NSC pool in PD mouse brain, and supports use of the disclosed compositions and method to eliminate the toxic proteins including aSyn (FIG. 4A-4C) and to restore functional neurons (FIGS. 5A-5B, 7A-7B) by co-administrations of neuroprotective and neurogenerative gangliosides in disease brains to achieve an efficacious and safe therapy.

Figures 8A, 8B, 8C, 8D, 8E:
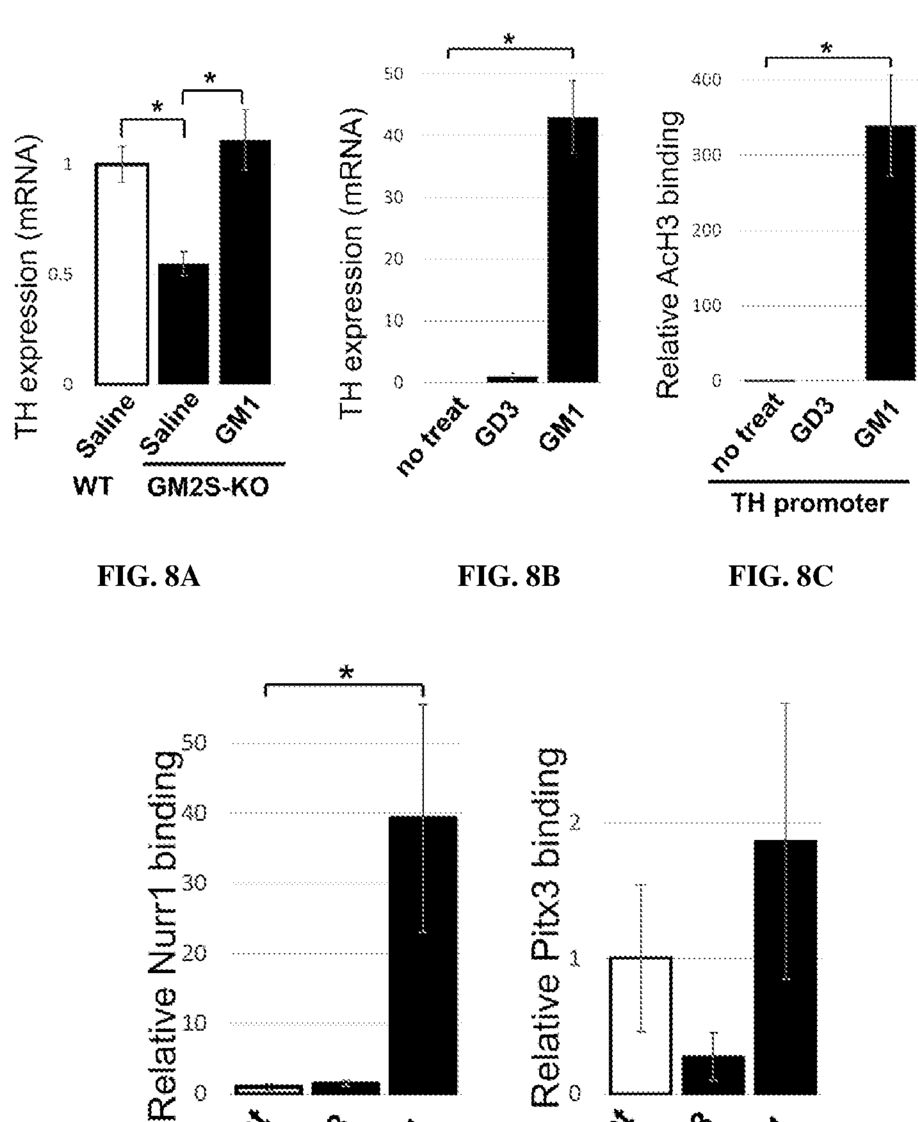
FIGS. 8A-8E are bar graphs showing ectopic GM1 induces epigenetic activation of the TH gene via recruitment of dopaminergic transcription factor Nurr1.

Example 6: GM1 Induces Epigenetic Activation of the TH Gene via Recruitment of Nurr1, an Essential Transcription Factor for Dopaminergic Neurons Interestingly, intranasal administration of GM1 for 28 days could restore the normal TH expression (FIG. 8A). These data indicate that GM1 is an important regulatory factor in modulating TH gene expression. Next, dopaminergic neuron-specific gene expression was analyzed utilizing Neuro 2a cells after treatment with GM1 or GD3. TH expression was not detected in untreated cells, whereas GM1 dramatically increased the TH expression (FIG. 8B). A chromatin immunoprecipitation (ChIP) assay showed that ectopic GM1 significantly induced epigenetic activation of the TH gene, including augmentation of acetylated histone H3 (FIG. 8C). Moreover, GM1 remarkably recruited the dopaminergic neuron-associated transcription factor, Nurr1, on the TH promoter region (FIG. 8D). This result demonstrates that GM1 promotes the interaction of Nurr1 with the TH gene promoter for activating its gene expression. In addition, GM1 also recruited Pitx3, a important transcription factor for the survival of midbrain dopaminergic neurons (FIG. 8E).

To further investigate the significance of nuclear GM1, cells were treated with photoactivatable and clickable GM1 (pacGM1). pacGM1 in isolated nuclei was visualized using click chemistry-mediated tagging with fluorophores. Results that exogenous pacGM1 is indeed delivered into the nucleus. Recently, proximity ligation assays (PLAs) have been developed to detect the formation of lipid-protein interaction by immunohistochemistry. Each PLA probe contains a unique short DNA strand attached to it. If the PLA probes are in close proximity (<40 nm), the DNA strands interact and generate circle-forming DNA used for enzymatic ligation. The ligated DNA is amplified via rolling circle amplification using a polymerase. A several hundred-fold replication of the DNA circle labels complementary oligonucleotide probes that yield high intensity of fluorescence. Using this technology, nuclei from WT mice were isolated and PLAs were performed to detect GM1 and the acetylated histone complex. The results PLA signals indicated that GM1 is indeed co-localized with acetylated histone H3, i.e., GM1 is localized on active chromatin in the nucleus (1.94±0.297 PLA signals in the nucleus). The results of both experiments clearly indicate that GM1 is localized in the nucleus and that GM1 interacts with transcriptionally active histones. Nuclear GM1 modulates gene transcription to sustain functional neurons to ameliorate aSyn toxicity. Further experiments are in progress to elucidate the detailed mechanisms. Nevertheless, it is safe to conclude that intranasal gangliosides reduce aSyn toxicity and that GM1 epigenetically sustains dopaminergic neurons.

Example 7: Gangliosides can Enhance Cognitive Function

Figures 9A, 9B:
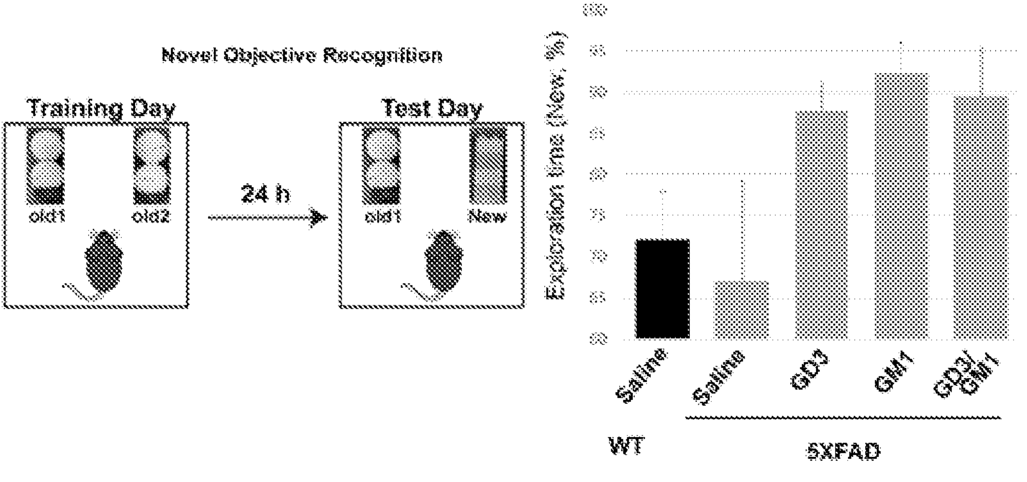
FIGS. 9A and 9B illustrate the memory function of intranasal ganglioside treatments.

Gangliosides (5 mg/kg/day), GD3, GM1, or GD3-GM1 (GD3 for 4 weeks and GM1 for 4 week) were administered into 2-month-old 5XFAD mice for 8 weeks. To assess the effect of intranasal ganglioside treatment on cognitive function, mice were tested using the novel object recognition test (FIG. 9A). Results show that intranasal ganglioside treatment promoted hippocampal-dependent recognition memory, as evidenced by a significant increase in preference to explore novel objects compared with non-treated mice (FIG. 9B). These findings indicate that intranasal ganglioside has an important role to enhance hippocampal-dependent learning and memory.

Example 8: Gangliosides can Improve Olfaction Deficiency

Figures 10A, 10B:
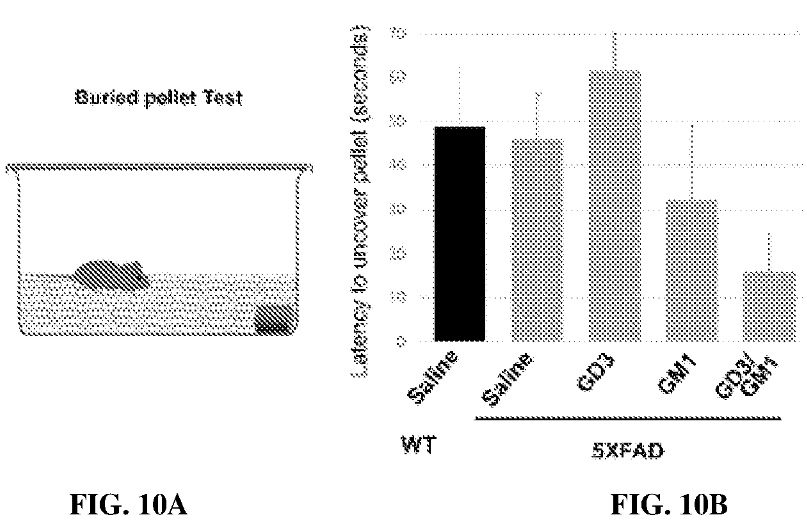
FIGS. 10A and 10B show olfactory function is enhanced by intranasal ganglioside treatments.

To detect olfaction deficiency, the buried pellet test was assessed (FIG. 10A). Bedding tips were set to 3 cm height. The time until mice uncover the food pellet was measured. Intranasal GM1 infusion enhance olfactory function. The combinational infusion (GD3 and GM1) had a more than additive effect to promote olfactory function (FIG. 10B). It is believed that GD3 maintains stemness and inhibits further neuronal differentiation such as olfactory neurons. That might be why GD3 alone could not enhance olfactory function.

Example 9: Gangliosides can Strengthen Bone Density

Figures 11A, 11B, 11C:
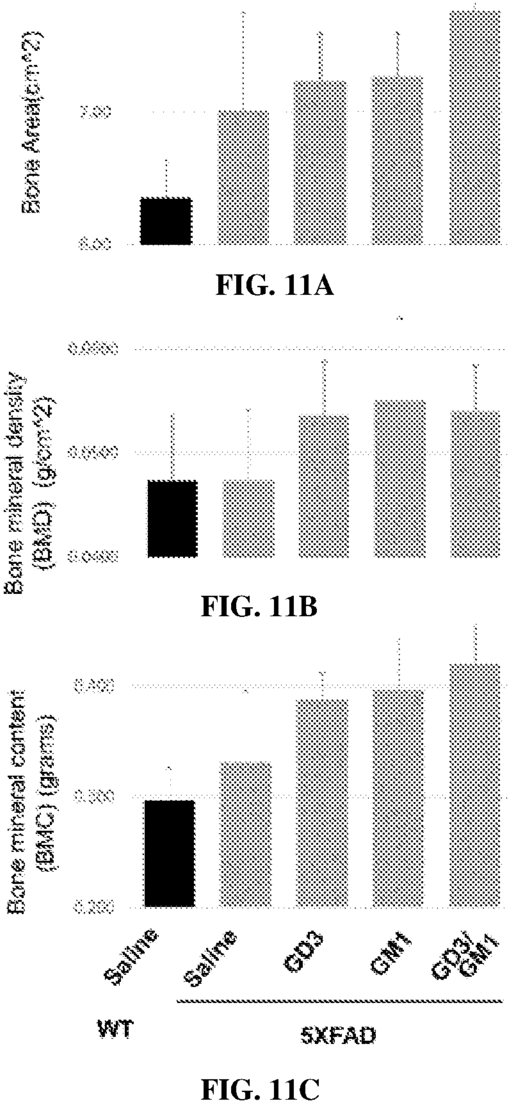
FIGS. 11A-11C show bone density is strengthen with intranasal ganglioside treatments.

Bone loss often accelerates with neurodegenerative diseases and during aging. Protecting from bone loss would be complementary to treatments for neurodegenerative diseases. Body composition analyses were measured by dual-energy X-ray absorptiometry (DXA; Kubtec Digimus, KUB Technologies, Stratford, CT, USA). Bone area (cm2), Bone mineral content (BMC, grams) and bone mineral density (BMD, g/cm2) were calculated for the whole body (FIGS. 11A-11C) using the manufacturer's analysis software (Kubtec Digimus). Interestingly, intranasal ganglioside treatments increase bone density. Increasing bone density in patients with neurodegenerative diseases, would decrease risk of fracture and increase the quality of life.

Although intranasal ganglioside administration increased memory and olfactory functions and bone density, the differences between WT and 5XFAD were not statistically significant at 2-month-old.

Example 10: GD3S-KO Mice Display Olfactory Impairments

Figure 12:
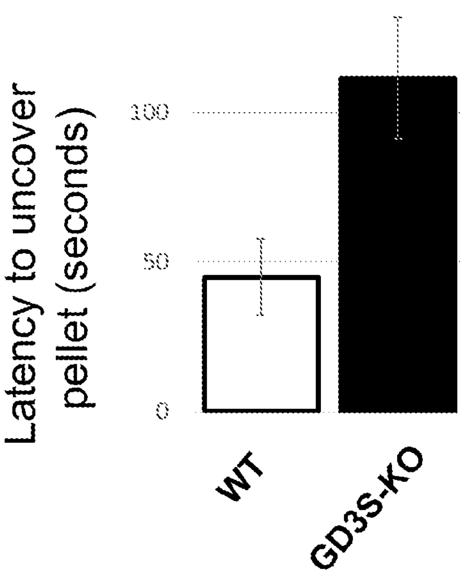
FIG. 12 is a bar graph showing latency to uncover pellets in wildtype and GD3S knockout mice.

The buried pellet test, which relies on the animal's natural tendency to use olfactory cues for foraging, is used to confirm ability to smell (FIG. 10A). The time until mice uncover the food pellet in bedding tips was measured. GD3S-KO mice took significantly longer time to find the buried pellet than WT (n=8-9 mice/group). Thus, GD3 has important role in olfactory function (FIG. 12).

Example 11: GM1 is Important to Prevent from Schizophrenia

Figure 13A:
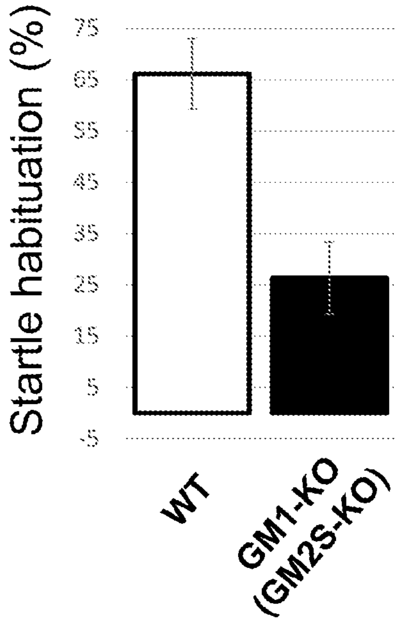
FIGS. 13A and 13B are bar graphs showing startle habitation (%) (13A) and PPI (%) in wildtype and GM1 (GM2S) knockout mice.
Figure 13B:
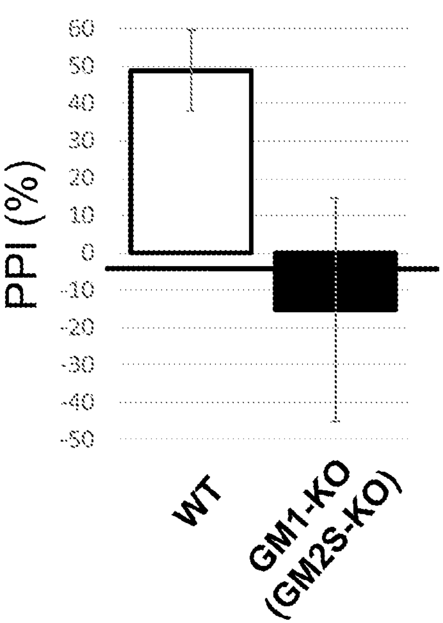
Figure 14:
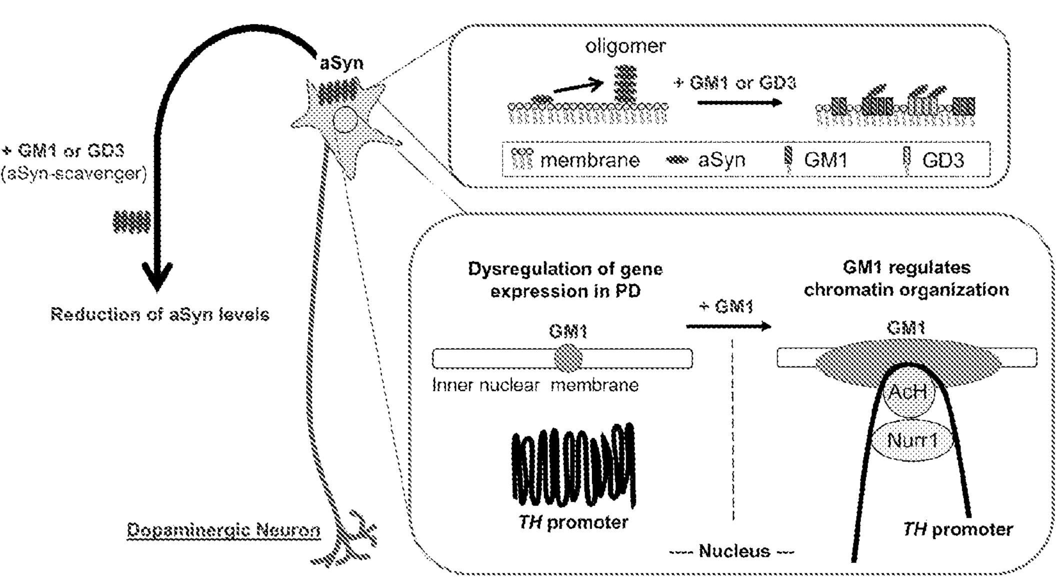
FIG. 14 is a schematic diagram of intranasal ganglioside therapy. Gangliosides prevent aSyn accumulation, and a supportive ganglioside composition will reduce aSyn neurotoxicity. GM1 strongly inhibits, and GD3 partially inhibits, aSyn accumulation. GM1 facilitates binding of acetylated histones (AcHs) and Nurr1 transcription factor on the TH promoter to increase TH expression via opening chromatin. The nuclear GM1-lipid domains may serve as a docking site at the nuclear periphery for specific active chromatins for dopaminergic neurons and for maintaining neuronal functions. Thus, ganglioside therapy is a two-pronged approach that effectively treats PD by decreasing cytotoxic aSyn and sustaining the function of dopaminergic neurons.

Numerous studies have demonstrated habituation and PPI deficits in schizophrenic patients. It has been discovered that GM1-KO mice have schizophrenia-like symptoms. Startle response to acoustic stimuli, its habituation, and Pre-pulse inhibition (PPI) were examined in these mice. FIG. 13A shows that the decrease of the acoustic startle response magnitude upon repeated presentation of the same stimulus. About PPI (FIG. 13B), the suppression of the startle response was detected when a weak prestimulus precedes the strong startling stimulus. Both habituation and PPI are disrupted in patients suffering from schizophrenia. Thus, these finding indicates that GM1 has an important role to prevent from schizophrenia-like symptoms.

Example 12: GD3 is Important to Repair Eye Injury

The effects of gangliosides during neural regeneration in the retina is being studied. NMDA (40 mM in 0.9% saline) was administrated by intravitreous injection using 33 gauge needle to WT or GD3S-KO mice. After 30 days post injury, regeneration capability was observed. GD3 deficient mouse had more tissue damage and delayed recovery. This result is consistent with the conclusion that GD3 plays an important role in regulating the visual system and its resiliency.

Summary

Methods and compositions to inhibit neurodegenerative disease development by removing neurotoxic proteins (aSyn or Aβs) from neurodegenerative brains, and by restoring neurogenesis in chronic damaged brains are provided. Remarkably, gangliosides GM1, GD3 and others are capable of forming complexes with aSyn or Aβs to eliminate toxic effects from cells. Results show that administrated neuroprotective gangliosides possess physiological properties to ameliorate the adverse effects of cytotoxic proteins, and regulates adult neurogenesis to maintain healthy brain. Thus, changes in ganglioside composition are indicative of alterations in cellular events in pathological conditions. The research shows that neuroprotective and neuroregenerative gangliosides prevent mammalian brains from neurodegenerative pathogenesis. Activation and promotion of adult neurogenesis by two gangliosides (GD3, GM1) in the brain for preventing AD or PD development from healthy brain is a desirable approach. Neuroprotective and neuroregenerative ganglioside composition is believed to increase resilience to AD or PD pathogenesis by way of maintaining neurogenesis and lowering toxic protein concentrations. The disclosed compositions and methods are believed to be an effective and safe therapeutic strategy for delaying or even preventing AD or PD progression from healthy aging brains by employing neuroprotective gangliosides.

Loss of neurogenic capability occurs in chronical neurodegenerative brain, and it is believed that an accelerated loss of NSC pool is one mechanism for transition from healthy brain to neurodegenerative brains. There is a lack of strategies to block the transition to neurodegenerative brains from healthy aging brains. Activation of adult neurogenesis is known to be promoted by a number of means, for example, exercise, as advocated by many investigators, or neurotrophic factors, such as NGF, EGF, FGF, BDNF, GDNF, and IGF (Mu & Gage, *Molecular neurodegeneration,* 6:85. PubMed PMID: 22192775. Pubmed Central PMCID: 3261815 (2011), Sleiman et al., *eLife,* 5. PubMed PMID: 27253067. Pubmed Central PMCID: 4915811 (2016)). The disclosed compositions and methods offer an appealing alternative or supplement to prevent healthy aging brains from neurodegenerative progression by employing neuroprotective and neuroregenerative gangliosides.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method for treating one or more of the symptoms or processes of neurodegeneration in a subject in need thereof comprising intranasally administering to the subject an effective amount of ganglioside GD3.

2. The method of claim 1, wherein GD3 is administered in an effective amount to increase the number of neural stem cells (NSCs) in the brain of the subject.

3. The method of claim 1, further comprising administering to the subject GM1 in an effective amount to increase neuronal differentiation in the brain of the subject.

4. The method of claim 3, wherein GD3 is administered prior to GM1.

5. The method of claim 4, wherein administration of the GM1 is after GD3 has begun increasing the number of neural stem cells (NSCs), and wherein GM1 increases differentiation of the NSCs.

6. The method of claim 3, comprising two or more administrations of GD3 and/or GM1.

7. The method of claim 6, comprising concurrent, sequential and overlapping, and/or sequential and non-overlapping administration of GM1 and GD3.

8. The method of claim 1, wherein the amount of GD3 administered is effective to increase one or more of bone density, bone mineral content or bone area in the subject relative to an untreated control.

9. The method of claim 1, wherein the amount of GD3 administered is effective to treat olfactory dysfunction in the subject relative to an untreated control.

10. The method of claim 1, wherein the neurodegeneration comprises damage or deterioration of neurons.

11. The method of claim 10, wherein the subject suffers from neurodegenerative disease or disorder, a mental disorder, or a neuronal disease or injury to the head or neck optionally to the eyes, nose, spine, or brain.

12. The method of claim 3, wherein the subject suffers from a mental disorder is depression, and wherein the administering comprises administration of GD3 followed by administration of GM1.

13. The method of claim 11, wherein the subject suffers from a disease or injury of the eye, optionally wherein the disease or injury comprises retinal injury or retinal degeneration.

14. The method of claim 11, wherein the subject has suffered a traumatic brain injury.

15. The method of claim 11, wherein the subject suffers from olfactory impairment.

16. The method of claim 1, wherein the subject does not yet suffer from damage or deterioration of neurons.

17. The method of claim 1, wherein the method reduces formation of existing cytotoxic proteins amyloid β-peptide (Aβ) and alpha-synuclein (aSyn).

18. A method of treating neurodegeneration and/or neurological injury of the eye(s) of a subject in need thereof comprising administering an effective amount of ganglioside GD3, and optionally administering an effective amount of ganglioside GM1, into the eye(s) of the subject.

19. The method of claim 18, wherein the ganglioside(s) are present in an ocular formulation selected from solutions, suspensions, ointments, creams, or solid inserts.

* * * * *